United States Patent
Kaempfer et al.

(10) Patent No.: US 11,613,565 B2
(45) Date of Patent: Mar. 28, 2023

(54) ISOLATED PEPTIDES DERIVED FROM THE B7 LIGAND DIMER INTERFACE AND USES THEREOF

(71) Applicant: YISSUM RESEARCH DEVELOPMENT COMPANY OF THE HEBREW UNIVERSITY OF JERUSALEM LTD., Jerusalem (IL)

(72) Inventors: Raymond Kaempfer, Jerusalem (IL); Revital Levy, Zur Hadassa (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 16/747,687

(22) Filed: Jan. 21, 2020

(65) Prior Publication Data

US 2020/0148741 A1    May 14, 2020

Related U.S. Application Data

(62) Division of application No. 15/558,080, filed as application No. PCT/IL2016/050285 on Mar. 16, 2016, now Pat. No. 10,584,157.

(60) Provisional application No. 62/133,639, filed on Mar. 16, 2015.

(51) Int. Cl.
  *C07K 14/705* (2006.01)
  *A61K 38/00* (2006.01)

(52) U.S. Cl.
  CPC ........ *C07K 14/70532* (2013.01); *A61K 38/00* (2013.01); *Y02A 50/30* (2018.01)

(58) Field of Classification Search
  CPC ... C07K 14/70532; A61K 38/00; Y02A 50/30
  See application file for complete search history.

(56) References Cited

U.S. PATENT DOCUMENTS

| | | | |
|---|---|---|---|
| 6,130,316 A | 10/2000 | Freeman et al. | |
| 6,294,660 B1 | 9/2001 | Sharpe et al. | |
| 7,432,351 B1 | 10/2008 | Chen | |
| 2011/0223188 A1* | 9/2011 | Langermann | A61P 31/16 435/243 |
| 2014/0220012 A1 | 8/2014 | Noelle et al. | |

FOREIGN PATENT DOCUMENTS

| | | | | |
|---|---|---|---|---|
| WO | WO-9710839 A1 * | 3/1997 | ....... | C07K 14/70503 |
| WO | WO-9858965 A2 * | 12/1998 | ........... | A61K 39/395 |
| WO | 2004087196 A2 | 10/2004 | | |

OTHER PUBLICATIONS

Yang et al, Novel oxytocin receptor agonists and antagonists: a patent review (2002-2013), Expert Opin. Ther. Patents, 2014, 24, pp. 29-46.*

Schwartz, J.C., Zhang, X., Fedorov, A.A., Nathenson, S.G., and Almo, S.C. (2001). Structural basis for co-stimulation by the human CTLA-4/B7-2 complex. Nature 410, 604-608.

Riley, J.L., and June, C.H. (2005) The CD28 family: a T-cell rheostat for therapeutic control of T-cell activation. Blood 105, 13-21.

Collins, A.V., Brodie, D.W., Gilbert, R.J., Iaboni, A., Manso-Sancho, R., Walse, B., Stuart, D.I., van der Merwe, P.A., and Davis, S.J. (2002). The interaction properties of costimulatory molecules revisited. Immunity 17, 201-210.

Greenwald, R.J., Freeman, G.J., and Sharpe, A.H. (2005). The B7 family revisited. Annu. Rev. Immunol. 23, 515-548.

Bhatia, S., Edidin, M., Almo, S.C., and Nathenson, S.G. (2006). B7-1 and B7-2:similar costimulatory ligands with different biochemical, oligomeric and signaling properties. Immunol. Lett. 104, 70-75.

Marrack, P., Blackman, M., Kushnir, E., and Kappler, J. (1990). The toxicity of staphylococcal enterotoxin B in mice is mediated by T cells. J. Exp. Med. 171, 455-464.

Miethke, T., Wahl, C., Heeg, K., Echtenacher, B., Krammer, P.H., and Wagner, H. (1992). T cell-mediated lethal shock triggered in mice by the superantigen staphylococcal enterotoxin B: critical role of tumor necrosis factor. J. Exp. Med. 175, 91-98.

Leder, L. et al. (1998). A mutational analysis of the binding of staphylococcal enterotoxins B and C3 to the T cell receptor beta chain and major histocompatibility complex class II. J. Exp. Med. 187, 823-833

(56) References Cited

OTHER PUBLICATIONS

GenPept Accession No. EAW79564 for CD80 antigen (CD28 antigen ligand 1, B7-1 antigen), isoform CRA_a, downloaded from ncbi.nlm.nih.gov/protein/EAW79564 on Jan. 1, 2018.
Mu et al., Mycoplasma superantigen initiates a TLR4-dependent TH17 cascase that enhances arthristis after blocking B7-1 in Mycoplasma arthritidis-infected mice, Cellular Microbiology, 16(6):896-911 (2014).
Davenport et al., Endothelin, Pharmacol Rev, 2016, 68, pp. 357-418.
Human Glucagon, from https://www.genscript.com/peptide/RP10772-Glucagon_1_29_Human.html, pp. 1-3, accessed Jan. 7, 2019.
Levy et al., Superantigens hyperinduce inflammatory cytokines by enhancing the B7-2/CD28 costimulatory receptor interaction, PNAS, E6437-E6446, published online Oct. 5, 2016.
Andreas O. Doesch et al., "Inhibition of B7-1 (CD80) by RhuDex® reduces lipopolysaccharide-mediated inflammation in human atherosclerotic lesions", Drug Design, Development and Therapy, Jan. 5, 2014, p. 447, only p. 447.

\* cited by examiner

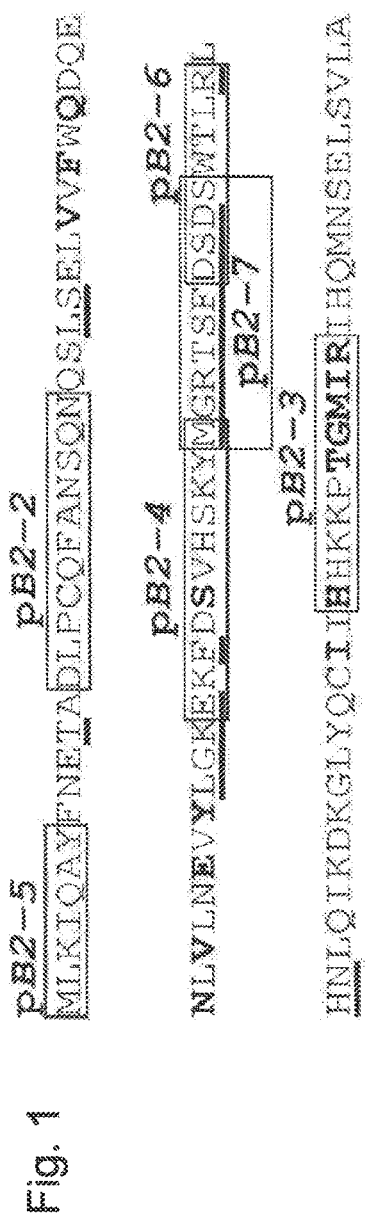
Fig. 1
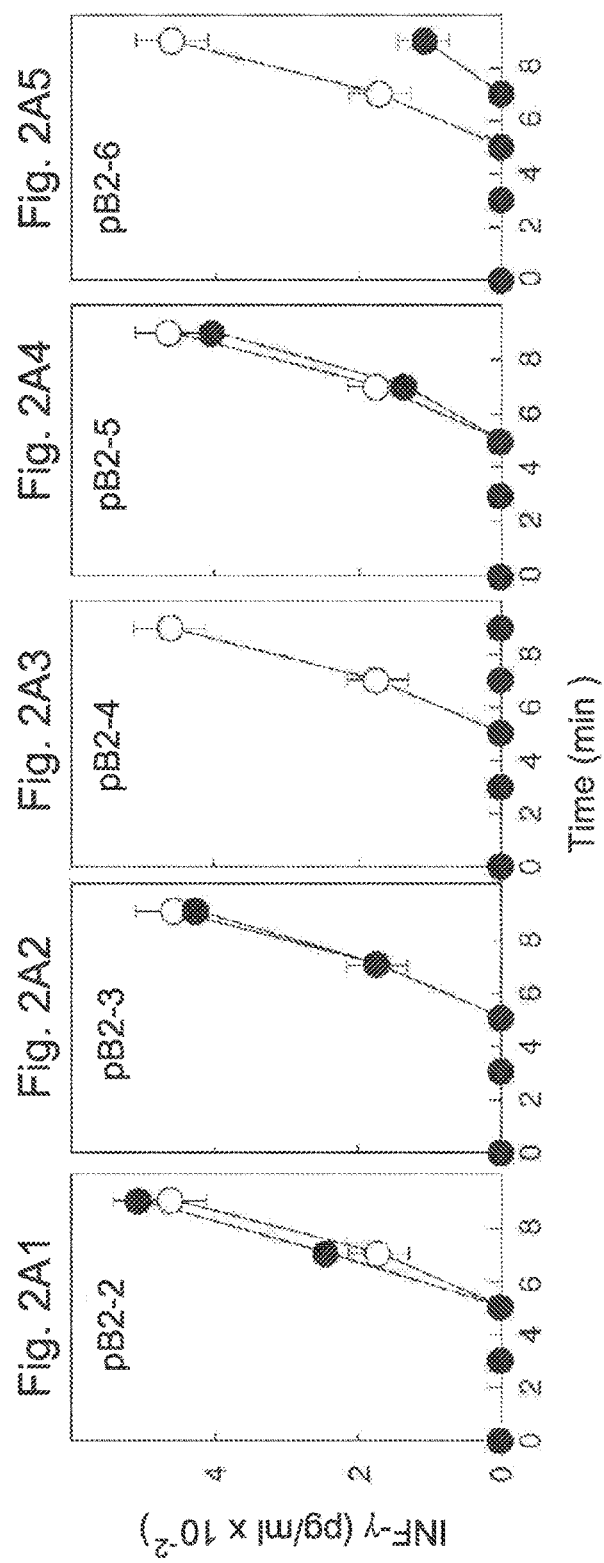
Fig. 2A1 pB2-2
Fig. 2A2 pB2-3
Fig. 2A3 pB2-4
Fig. 2A4 pB2-5
Fig. 2A5 pB2-6
Time (min)
INF-γ (pg/ml x $10^{-2}$)

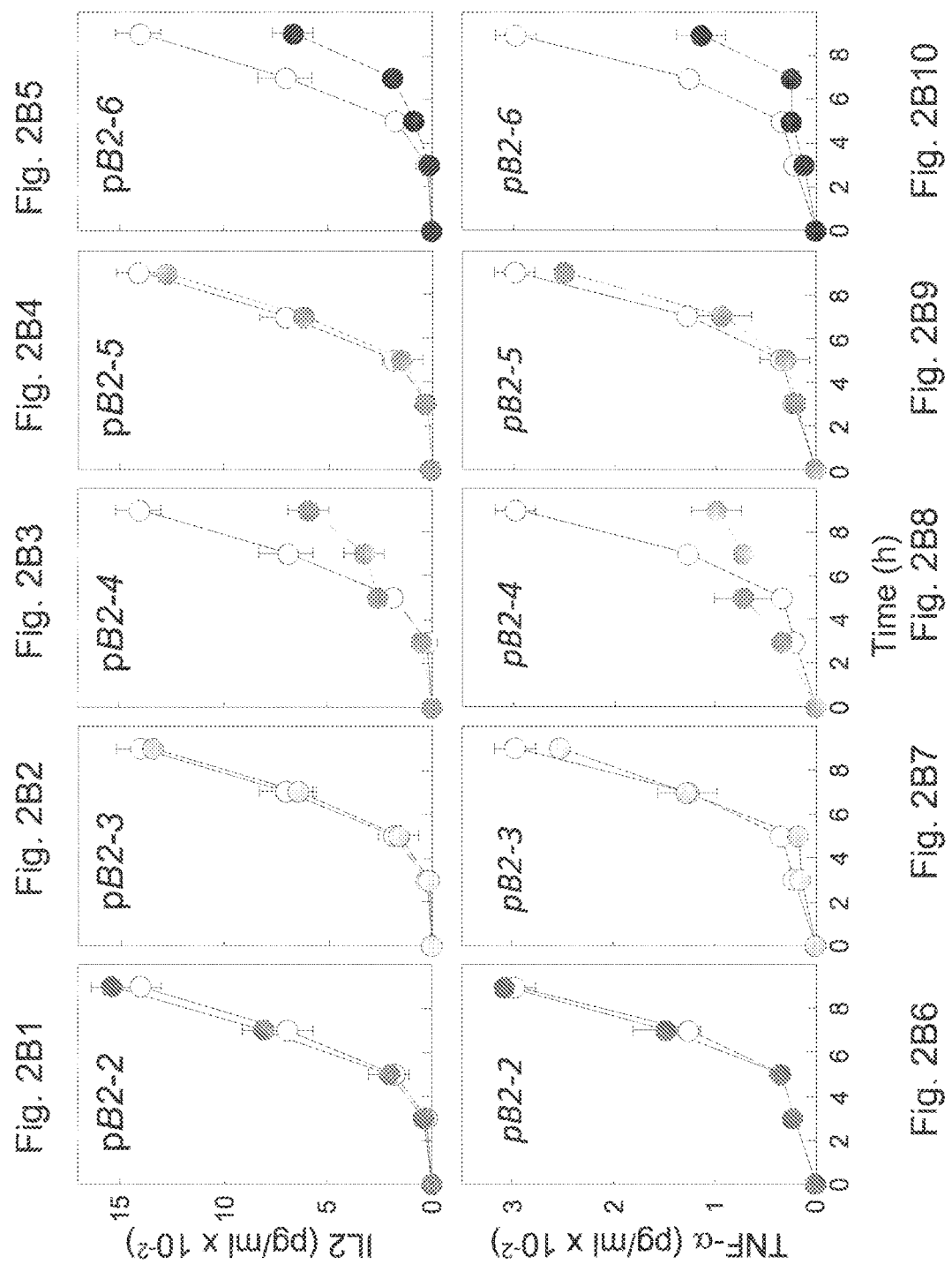

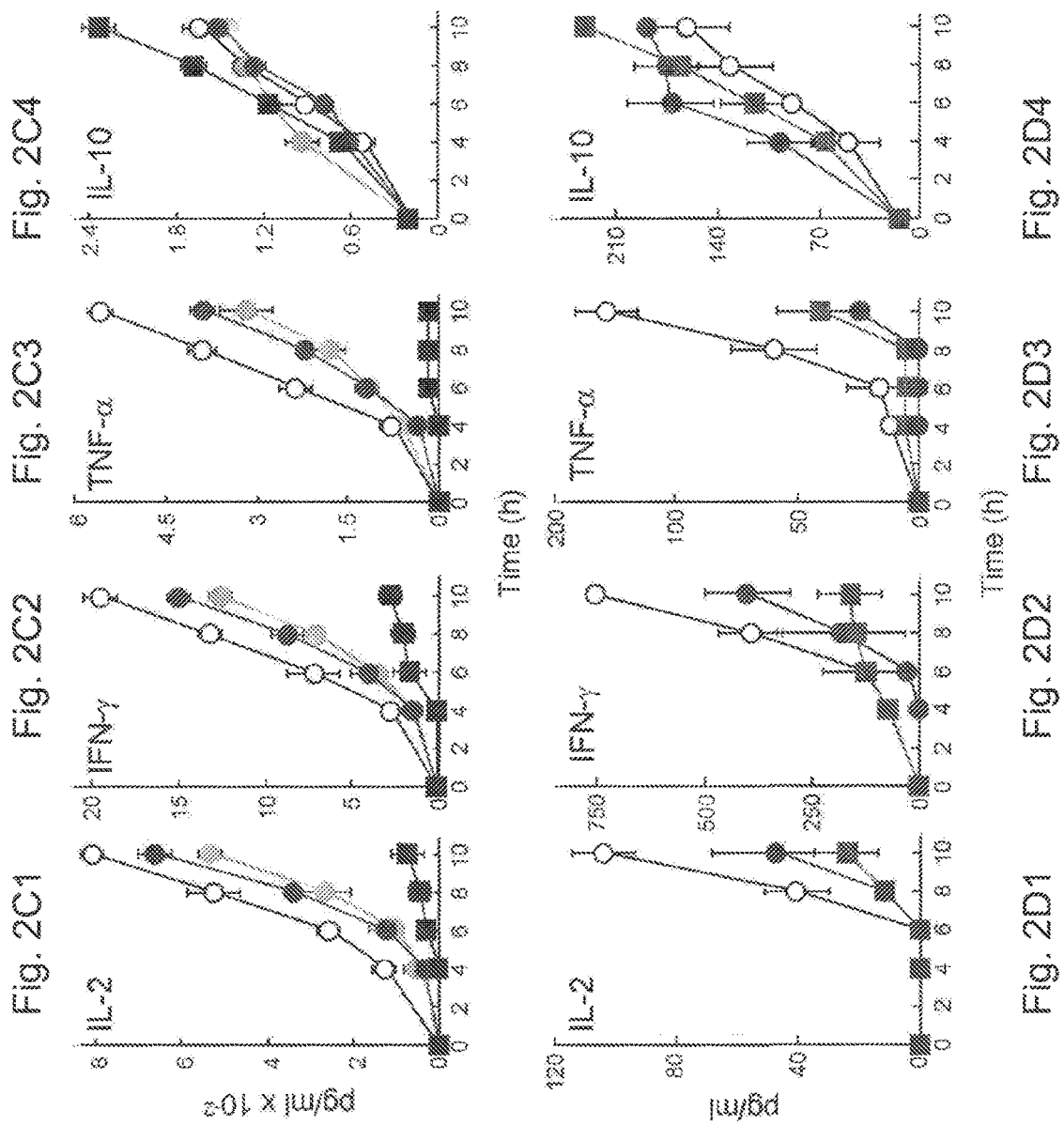

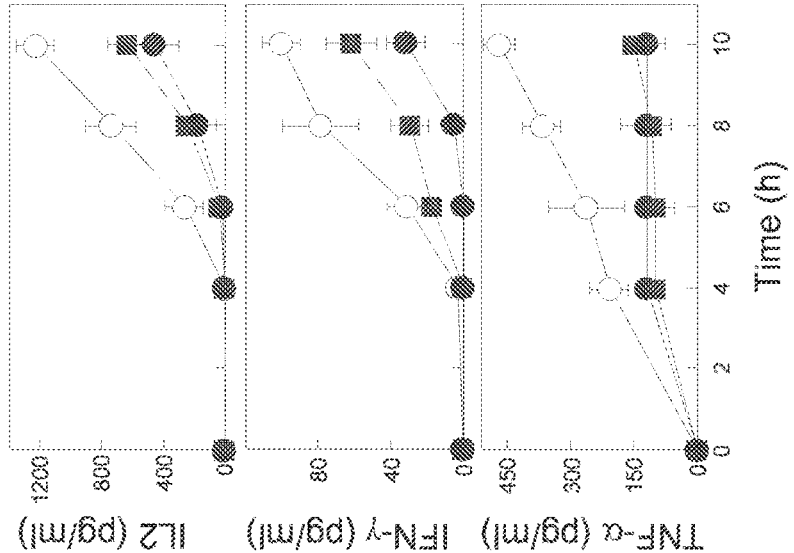
Fig. 2E5, Fig. 2E6, Fig. 2E7, Fig. 2E1, Fig. 2E2, Fig. 2E3, Fig. 2E4

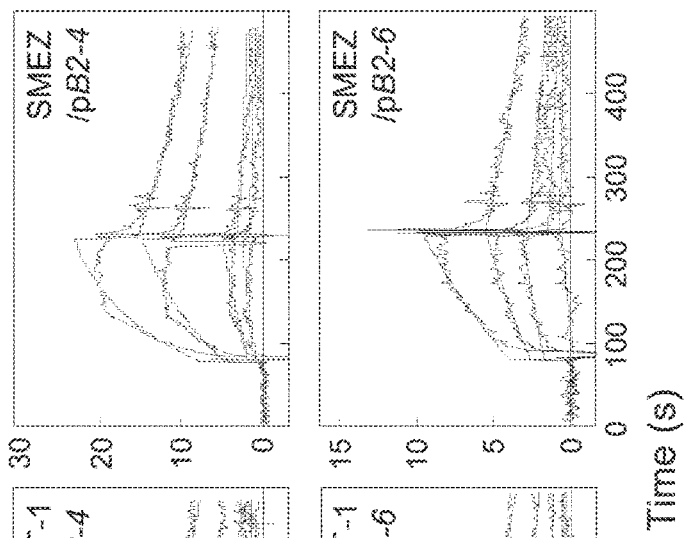
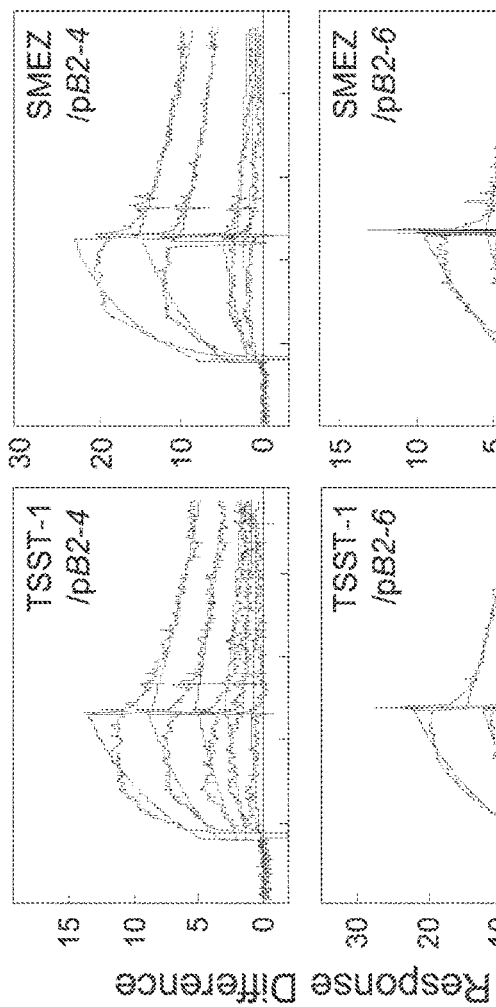
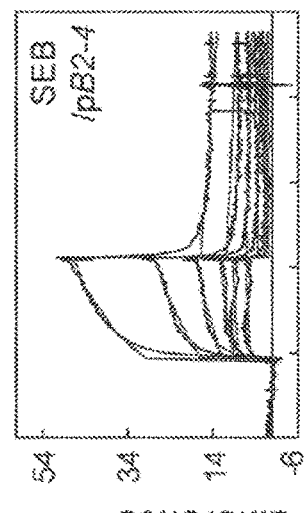

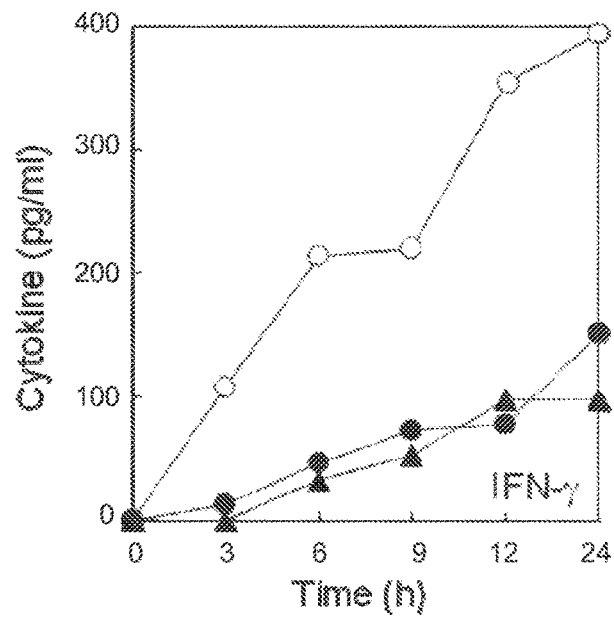 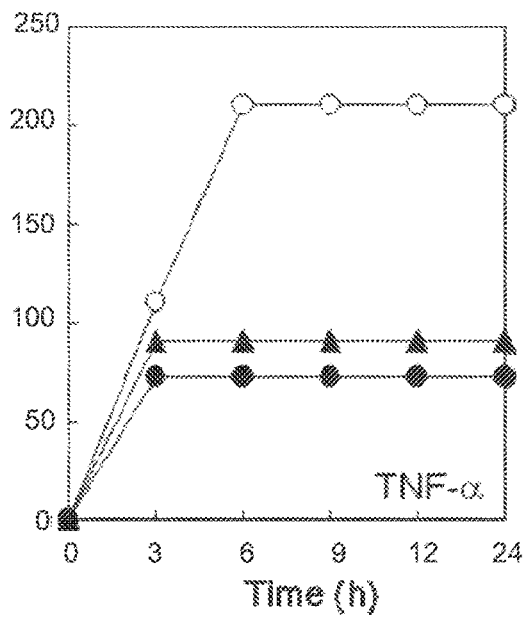
Fig. 7A  Fig. 7B
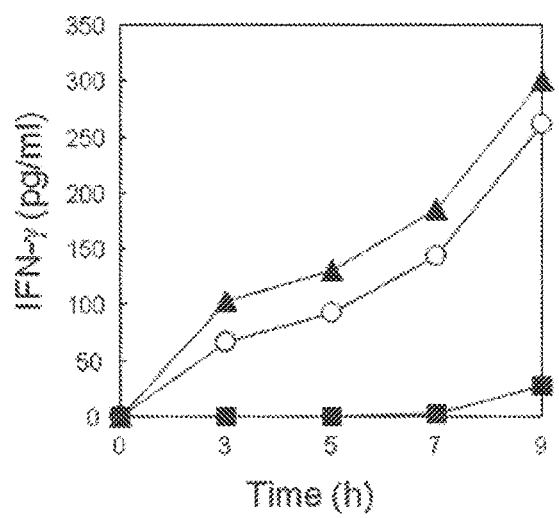 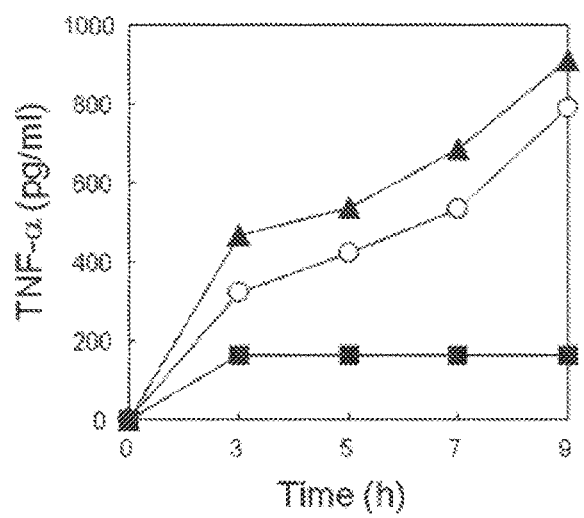
Fig. 8A  Fig. 8B

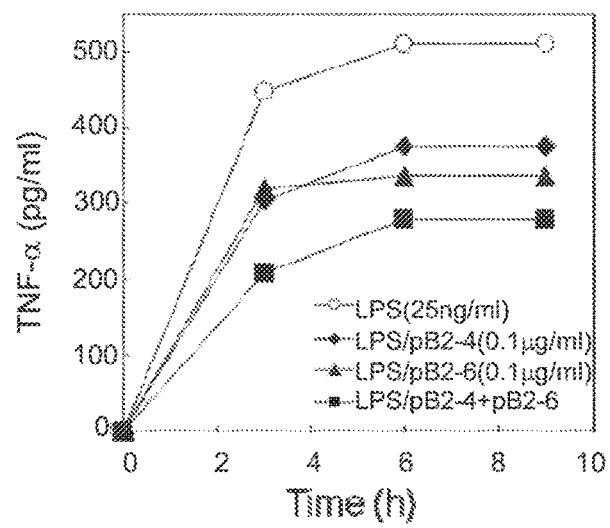
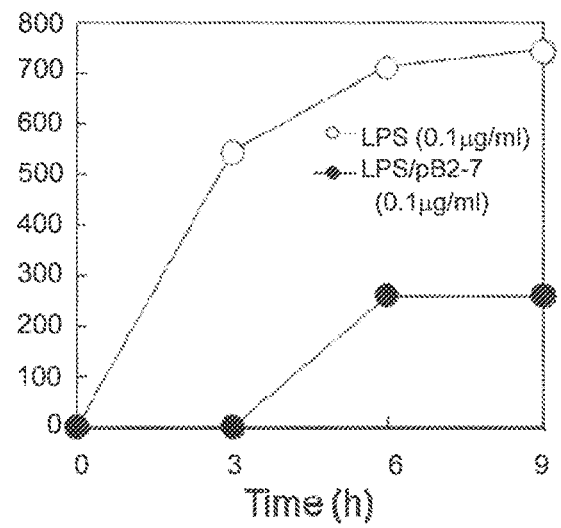
Fig. 9A        Fig. 9B
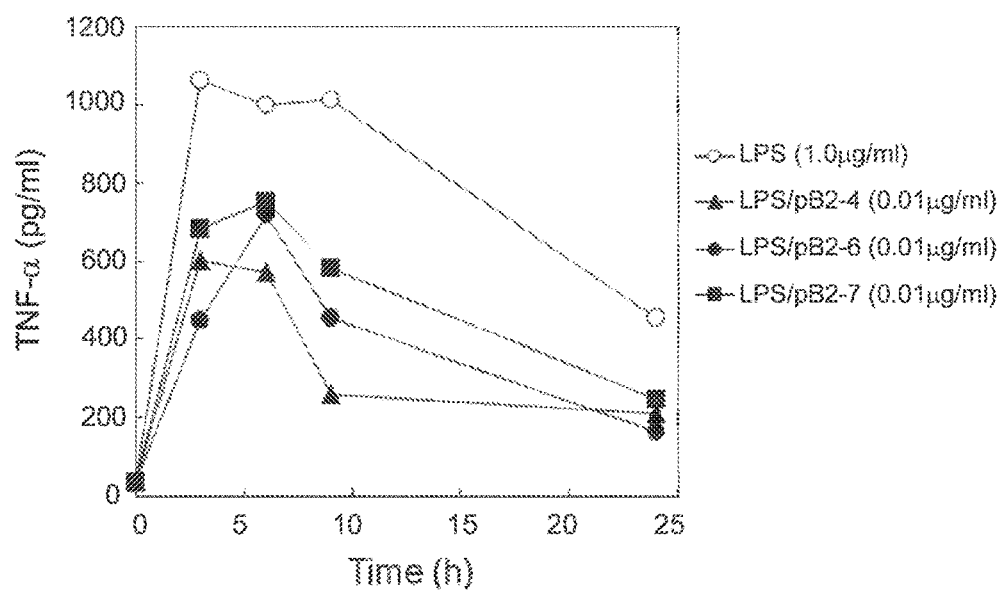
Fig. 10

SEQ ID NO:57  hB7-1  MN---IWPEYKNRTIFDITNNLSIV
                     |    pB1-4      |    pB1-6   |

SEQ ID NO:57  hB7-1  MN---IWPEYKNRTIFDITNNLSIV
                              |  pB1-7  |

SEQ ID NO:57  hB7-1  MN---IWPEYKNRTIFDITNNLSIV
                            |  pB1-8  |

Fig. 11

SEQ ID NO:58  hB7-2  EKFDSVHSKYMGRTSFDSDS-WTLR
SEQ ID NO:57  hB7-1  MN---IWPEYKNRTIFDITNNLSIV

Fig. 12

ISOLATED PEPTIDES DERIVED FROM THE B7 LIGAND DIMER INTERFACE AND USES THEREOF

The Sequence Listing in ASCII text file format of 22,919 bytes in size, created on Jan. 21, 2020, with the file name "2020-01-21SequenceListing_KAEMPFER20B," filed in the U.S. Patent and Trademark Office on Jan. 21, 2020, is hereby incorporated herein by reference.

TECHNOLOGICAL FIELD

Disclosed are peptides derived from the dimer interface of the B7 ligands. Specifically, the disclosure pertains to novel isolated, non-naturally occurring peptides, compositions comprising thereof and methods of treatment employing the same. Specific compositions and methods relate to treatment of infections induced by Gram positive and Gram negative bacteria and bacterial components thereof.

BACKGROUND ART

References considered to be relevant as background to the presently disclosed subject matter are listed below:
[1] Schwartz, J. C., Zhang, X., Fedorov, A. A., Nathenson, S. G., and Almo, S. C. (2001). Structural basis for co-stimulation by the human CTLA-4/B7-2 complex. Nature 410, 604-608.
[2] Sharpe, A. H., and Freeman, G. J. (2002). The B7-CD28 superfamily. Nat. Rev. Immunol. 2, 116-126.
[3] Riley, J. L., and June, C. H. (2005). The CD28 family: a T-cell rheostat for therapeutic control of T-cell activation. Blood 105, 13-21.
[4] Collins, A. V., Brodie, D. W., Gilbert, R. J., Iaboni, A., Manso-Sancho, R., Walse, B., Stuart, D. I., van der Merwe, P. A., and Davis, S. J. (2002). The interaction properties of costimulatory molecules revisited. Immunity 17, 201-210.
[5] Greenwald, R. J., Freeman, G. J., and Sharpe, A. H. (2005). The B7 family revisited. Annu. Rev. Immunol. 23, 515-548.
[6] Bhatia, S., Edidin, M., Almo, S. C., and Nathenson, S. G. (2006). B7-1 and B7-2: similar costimulatory ligands with different biochemical, oligomeric and signaling properties. Immunol. Lett. 104, 70-75.
[7] Marrack, P., Blackman, M., Kushnir, E., and Kappler, J. (1990). The toxicity of staphylococcal enterotoxin B in mice is mediated by T cells. J. Exp. Med. 171, 455-464.
[8] Miethke, T., Wahl, C., Heeg, K., Echtenacher, B., Krammer, P. H., and Wagner, H. (1992). T cell-mediated lethal shock triggered in mice by the superantigen staphylococcal enterotoxin B: critical role of tumor necrosis factor. J. Exp. Med. 175, 91-98.
[9] Leder, L. et al. (1998). A mutational analysis of the binding of staphylococcal enterotoxins B and C3 to the T cell receptor beta chain and major histocompatibility complex class II. J. Exp. Med. 187, 823-833.
[10] Arad, G., Levy, R., Nasie, I., Hillman, D., Rotfogel, Z., Barash, U., Supper, E., Shpilka, T., Minis, A., and Kaempfer, R. (2011). Binding of superantigen toxins into the CD28 homodimer interface is essential for induction of cytokine genes that mediate lethal shock. PLoS Biol. 9, e1001149.
[11] WO 2004/087196.
[12] Arad, G., Levy, R., Hillman, D., and Kaempfer, R. (2000). Superantigen antagonist protects against lethal shock and defines a new domain for T-cell activation. Nat. Med. 6, 414-421.
[13] Ramachandran, G. et al. (2013). A peptide antagonist of CD28 signaling attenuates toxic shock and necrotizing soft-tissue infection induced by Streptococcus pyogenes. J. Infect. Dis. 207, 1869-1877.
[14] Guerrier-Takada, C., Eder, P. S., Gopalan, V., and Altman, S. (2002). Purification and characterization of Rpp25, an RNA-binding protein subunit of human ribonuclease P. RNA 8, 290-295.

These publications are referred to below by their above numbers. Acknowledgement of the above references herein is not to be inferred as meaning that these are in any way relevant to the patentability of the presently disclosed subject matter.

BACKGROUND

As a principal co-stimulatory receptor, CD28 is a critical regulator of the immune response (1-3). Expressed constitutively on T cells, CD28 is a homodimer that interacts with its B7 coligands, namely, B7-1 (CD80) and B7-2 (CD86), expressed on antigen-presenting cells. CD28/B7 interaction results in transducing the signal essential for an immediate T-cell response (2-4). CD28 coligand B7-2 (CD86) is expressed constitutively on antigen-presenting cells whereas B7-1 (CD80) is induced only later (4); hence, B7-2/CD28 interaction regulates early antigen signaling (5, 6).

B7-1 and B7-2 are glycoproteins, each consisting of single V-like and C-like immunoglobulin superfamily (IgSF) domains. Their ligands, CD28 and CTLA-4, are also structurally related and expressed at the cell surface as disulfide-linked homodimers of single V-like IgSF domains.

The inflammatory cytokine response is indispensable for protective immunity yet bacterial and viral infections often elicit an exaggerated response ('cytokine storm') which is harmful to the host. It is known that bacterial superantigens from Staphylococcus aureus and Streptococcus pyogenes induce toxic shock by activating an immune response, orders of magnitude beyond that elicited by regular antigens. It has been previously shown that superantigens exploit the main axis of T-cell activation by binding directly as intact proteins to most major histocompatibility class II (MHC-II) and T-cell receptor (TCR) molecules outside their antigen-binding domains, linking them and bypassing restricted presentation of conventional antigens which typically activate <1% of T cells, thereby activating up to 20-30% of T cells (7-9).

Moreover, T-cell activation by superantigens requires their direct binding to CD28 (10), the second signaling molecule mandatory for T-cell activation. This results in massive induction of inflammatory cytokines that mediate toxic shock, including interleukin-2 (IL2), interferon-γ (IFN-γ) and tumor necrosis factor (TNF).

There are ample examples for the harmful effects of superantigens. For example, the majority of human food poisoning cases, manifested by vomiting and diarrhea after ingestion, are caused by the enterotoxins (SEs) family of superantigens, secreted by S. aureus. Among the major serological types within the SEs family are SEA, SEB, SEE and SEG, where SEB has been also recognized as a leading cause of human cases of non-menstrual toxic shock syndrome that can accompany surgical or injurious wound infections, as well as viral infections of the respiratory tract. Notably, toxic shock syndrome, in its most severe form, causes shock and death.

Bacterial superantigens are thus known to induce a Th1 cytokine storm, causing toxic shock. The inventors have previously shown that mice were protected from lethal superantigen challenge by peptide mimetics of the CD28 dimer interface and by peptides selected to compete with the superantigen for its binding site in CD28 (10, 11).

Specifically, induction of human inflammatory cytokine gene expression by divergent superantigens may be inhibited by a short peptide that shows homology to a 12-amino-acid β-strand-hinge-α-helix superantigen domain, which is structurally conserved in superantigens yet remote from their MHC-II and TCR binding sites. Through this domain, essential for superantigen action (10, 12), superantigens engage CD28 directly at its homodimer interface (10). Blocking access of a superantigen to CD28, with peptide mimetics of the CD28 homodimer interface or the β-strand-hinge-α-helix superantigen domain, suffices to block signaling for overexpression of inflammatory cytokines in human peripheral blood mononuclear cells (PBMC) and to protect mice from lethal toxic shock (10, 12, 13).

GENERAL DESCRIPTION

The present disclosure provides an isolated and purified peptide comprising at least one amino acid residue of the crystallographic dimer interface within a region of the extracellular domain of human B7-2, said region consisting of the amino acid sequence denoted by SEQ ID NO:13, wherein said crystallographic dimer interface consists of amino acid residues Thr-11, Leu-26, Ser-27, Leu-46, Gly-47, Lys-48, Glu-49, Phe-51, Met-59, Gly-60, Arg-61, Thr-62, Ser-63, Phe-64, Asp-65, Ser-66, Asp-67, Arg-72, His-74 and Asn-75 of SEQ ID NO:13, wherein said isolated and purified peptide further comprises at least 2 additional amino acid residues at its C-terminus and/or N-terminus, wherein said additional amino acid residues are consecutive amino acid residues of SEQ ID NO:13 immediately adjacent to said at least one amino acid residue of said crystallographic dimer interface in SEQ ID NO: 13, wherein said isolated and purified peptide consists of from 3 to about 30 amino acid residues, and functional fragments and derivatives thereof. These peptides are also referred to herein as "hB7-2 mimetic peptides".

In some embodiments the isolated and purified peptide according to the present disclosure comprises said at least one amino acid residue of the crystallographic dimer interface within a region of the extracellular domain of human B7-2 and from 2 to about 8 said additional amino acid residues at its C-terminus and/or N-terminus, and functional fragments and derivatives thereof.

In other embodiments the isolated and purified peptide according to the present disclosure consists of an amino acid sequence selected from the amino acid sequences denoted by SEQ ID NO:11 (MGRTSFDSDS, also designated pB2-7), SEQ ID NO:5 (EKFDSVHSKYM, also designated peptide pB2-4) and SEQ ID NO:9 (DSDSWTLR also designated peptide pB2-6) and functional fragments and derivatives thereof.

By a further aspect the present disclosure provides an isolated and purified peptide comprising at least one amino acid residue of the crystallographic dimer interface within a region of the extracellular domain of human B7-1, said region consisting of the amino acid sequence denoted by SEQ ID NO: 14, wherein said crystallographic dimer interface consists of amino acid residues Val-15, Leu-29, Ala-30, Ser-48, Gly-49, Asp-50, Met-51, Lys-58, Asn-59, Arg-60, Thr-61, Ile-62, Phe-63, Asp-64, Ile-65, Thr-66, Val-72, Leu-74 and Ala-75 of SEQ ID NO:14, wherein said isolated and purified peptide further comprises at least 2 additional amino acid residues at its C-terminus and/or N-terminus, wherein said additional amino acid residues are consecutive amino acid residues of SEQ ID NO:14 immediately adjacent to said at least one amino acid residue of said crystallographic dimer interface in SEQ ID NO: 14, wherein said isolated and purified peptide consists of from 3 to about 30 amino acid residues, and functional fragments and derivatives thereof. These peptides are also referred to herein as "hB7-1 mimetic peptides".

In some embodiments the isolated and purified peptide according to the present disclosure comprises said at least one amino acid residue of the crystallographic dimer interface within a region of the extracellular domain of human B7-1 and from 2 to about 8 said additional amino acid residues at each of its C-terminus and/or N-terminus, and functional fragments and derivatives thereof.

In other embodiments the isolated and purified peptide according to the present disclosure consists of an amino acid sequence selected from the amino acid sequences denoted by SEQ ID NO:38 (MNIWPEYK, designated pB1-4), SEQ ID NO:40 (KNRTIFDITN, designated pB1-7), SEQ ID NO:42 (DITNNLSIV, designated pB1-6), SEQ ID NO:46 (SGDMNIWPEYKNRTIFDITNNLSIVILA) and SEQ ID NO:48 (YKNRTIFD, designated pB1-8) and functional derivatives thereof.

In further embodiments the functional derivative of the presently disclosed isolated and purified peptide is any one of:
i. said B7-2 mimetic peptide that is extended at the N terminus and/or the C terminus thereof by 1 to 4 consecutive amino acid residues present in immediately adjacent corresponding positions of the amino acid sequence denoted by SEQ ID NO: 13;
ii. said B7-2 mimetic peptide that is extended at the N terminus and/or the C terminus thereof:
  (a) by cysteine or by lauryl cysteine;
  (b) by an organic moiety that is not naturally occurring or by a synthetic amino acid residue;
  (c) by N-acetyl or lysyl-palmitoyl residue;
  (d) by hydrophobic amino acid residue(s) which may be naturally occurring or synthetic amino acid residues; or
iii. a dimer or multimer of any of the peptides of (i) and (ii);
iv. a constrained conformation of said B7-2 mimetic peptide;
v. any of said B7-2 mimetic peptides and their derivatives as defined in (i) to (iv), that is modified by at least one synthetic mutation selected from insertion, deletion, substitution, provided that the modified peptide comprises at least one amino acid residue of the said dimer interface;
wherein said derivative consists of from 3 to about 40 amino acid residues.

In still further embodiments the functional derivative of the presently disclosed isolated and purified peptide is any one of:
i. said B7-1 mimetic peptide that is extended at the N terminus and/or the C terminus thereof by 1 to 4 consecutive amino acid residues present in immediately adjacent corresponding positions of the amino acid sequence denoted by SEQ ID NO: 14;
ii. said B7-1 mimetic peptide that is extended at the N terminus and/or the C terminus thereof:
  (a) by cysteine or by lauryl cysteine;
  (b) by an organic moiety that is not naturally occurring or by a synthetic amino acid residue;
  (c) by N-acetyl or lysyl-palmitoyl residue;

(d) by hydrophobic amino acid residue(s) which may be naturally occurring or synthetic amino acid residues; or iii. a dimer or multimer of any of the peptides of (i) and (ii);

iv. a constrained conformation of said B7-1 mimetic peptide;

v. any of said B7-1 mimetic peptides and their derivatives as defined in (i) to (iv), that is modified by at least one synthetic mutation selected from insertion, deletion, substitution, provided that the modified peptide comprises at least one amino acid residue of the said dimer interface;

wherein said derivative consists of from 3 to about 40 amino acid residues.

In some aspects and embodiments the isolated and purified peptide as herein disclosed is extended at its N terminus and/or at its C terminus by a D-Ala amino acid residue.

In specific embodiments the isolated peptide according to the present disclosure is any one of a peptides consisting of the amino acid sequence (D-A)EKFDSVHSKYM(D-A) as denoted by SEQ ID NO:6 (also designated herein as peptide D-Ala-pB2-4), a peptide consisting of the amino acid sequence (D-A)DSDSWTLR(D-A) as denoted by SEQ ID NO: 10 (also designated herein as peptide D-Ala-pB2-6) and a peptide consisting of the amino acid sequence (D-A) MGRTSFDSDS(D-A) as denoted by SEQ ID NO: 12 (also designated herein as peptide D-Ala-pB2-7).

In other specific embodiments the isolated and purified peptide according to the present disclosure is any one of a peptide consisting of the amino acid sequence (D-A) MNIWPEYK(D-A) as denoted by SEQ ID NO: 39 (also designated D-Ala-pB1-4), a peptide consisting of the amino acid sequence (D-A)KNRTIFDITN(D-A) as denoted by SEQ ID NO:41 (also designated D-Ala-pB1-7), a peptide consisting of the amino acid sequence (D-Ala)DITNNLSIV (D-Ala) as denoted by SEQ ID NO:43 (also designated D-Ala-pB1-6), and a peptide consisting of the amino acid sequence (D-Ala)YKNRTIFD(D-Ala) denoted by SEQ ID NO:49 (also designated D-Ala-pB1-8).

The present disclosure further provides a pharmaceutical composition comprising as an active ingredient at least one isolated and purified peptide as herein defined, optionally further comprising a pharmaceutically acceptable carrier, diluent, adjuvant and/or excipient.

In some embodiments the pharmaceutical composition according to the present disclosure is for eliciting protective immunity against at least one of sepsis, toxic shock, septic shock, severe sepsis, incapacitation and resulting death, that are induced by a bacterial pathogen, a mixture of bacterial pathogens and/or a toxic bacterial component.

In other embodiments the pharmaceutical composition according to the present disclosure is for the treatment of at least one of a bacterial infection and acute inflammation associated therewith in a human subject.

In all aspects and embodiments the at least one of bacterial infection and acute inflammation associated therewith is induced by at least one of Gram-positive bacteria, Gram-negative bacteria and toxic bacterial components.

In all aspects and embodiments the Gram-negative bacteria are selected from the group consisting of proteobacteria, *Escherichia coli, Salmonella, Shigella, Enterobacteriaceae, Pseudomonas, Moraxella, Helicobacter, Bdellovibrio, Stenotrophomonas*, acetic acid bacteria, *Legionella*, alpha-proteobacteria, *Wolbachia*, Gram-negative cocci, *Neisseria* species, *Neisseria gonorrhoeae, Neisseria meningitidis, Moraxella catarrhalis*, Gram-negative *bacilli,*  *Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Acinetobacter baumannii, Francisella tularemia, Vibrio, vulnificus, cholerae, fluvialis, parahemolyticus, alginolyticus, Photobacter damsela, Aeromonas hydrophila, Clostridium perfringens, Clostridium histolyticum, Porphyromonas/prevotella* sp. *Prevotella Intermedia, Prevotella Buccae, Prevotella* sp., *Bacteroides uniformis* and NDM-1 bacterial strains, the Gram-positive bacteria are selected from the group consisting of Group A *streptococcus, S. pyogenes, S. pneumonia*, Group B strep, *Enterococcus faecalis*, Group D *streptococcus*, Group G *streptococcus, Streptococcus viridans, Streptococcus milleri, Propionibacterium* sp., *Enterococcus faecium, Peptostreptococcus* sp., *Streptococcus Microaerophilic, Lactobacillus* sp., *Staphylococcus Epidermis* and *Staphylococcus aureus*, and the toxic bacterial components are selected from the group consisting of exotoxins, endotoxins, superantigenic toxins, pathogen associated molecular patterns (PAMPs), Damage Associated Molecular Pattern molecules (DAMPs), lipopolysaccharides, peptidoglycans or toxic components thereof, molecules that are associated with groups of pathogens that are recognized by cells of the innate immune system and molecules that are associated with groups of pathogens that are recognized by Toll-like receptors (TLRs).

In some embodiments the at least one toxic bacterial component is a superantigenic toxin.

In other embodiments the pharmaceutical composition according to the present disclosure is for any one of oral administration and parenteral administration.

In all aspects and embodiments the parenteral administration as herein defined is any one of intravenous, intramuscular, intraperitoneal, intranasal, intrathecal subcutaneous injection or said administration is by inhalation.

The present disclosure further provides a peptide as herein defined for use in a method for eliciting in a human subject in need protective immunity against at least one of sepsis, toxic shock, septic shock, severe sepsis, incapacitation and resulting death, that are induced by a bacterial pathogen, a mixture of bacterial pathogens and/or a toxic bacterial component.

By another one of its aspects the present disclosure provides a peptide as herein defined for use in a method of treating at least one of bacterial infection and acute inflammation associated therewith in a human subject in need.

The present disclosure further provides a pharmaceutical composition as herein defined for use in a method for eliciting in a human subject in need protective immunity against at least one of sepsis, toxic shock, septic shock, severe sepsis, incapacitation and resulting death, that are induced by a bacterial pathogen, a mixture of bacterial pathogens and/or a toxic bacterial component.

By still another one of its aspects the presently disclosed subject matter provides a pharmaceutical composition comprising as an active ingredient at least one isolated and purified peptide as herein defined for use in a method of treating at least one of bacterial infection and acute inflammation associated therewith in a human subject in need, wherein said pharmaceutical composition optionally further comprises a pharmaceutically acceptable carrier, diluent, adjuvant and/or excipient.

The presently disclosed subject matter further provides a method for eliciting in a human subject in need protective immunity against at least one of sepsis, toxic shock, septic shock, severe sepsis, incapacitation and resulting death, that are induced by a bacterial pathogen, a mixture of bacterial pathogens and/or at least one toxic bacterial component, said method comprising administering to said subject an immunologically effective amount of a peptide as herein defined or of a pharmaceutically acceptable composition comprising the same.

In some embodiments the method of treating at least one of bacterial infection and acute inflammation associated therewith further comprises administering an additional therapeutic agent to said human subject in need.

In some embodiments the immunologically effective amount is from about 0.1 to about 60 μg/Kg body weight of said subject.

The present disclosure further provides a method of treating at least one of bacterial infection and acute inflammation associated therewith in a human subject in need, comprising administering to said subject a therapeutically effective amount of at least one peptide or a composition comprising the same as herein defined.

In some embodiments the therapeutically effective amount as herein defined is from about 0.1 to about 60 μg/Kg body weight of said subject.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1: Peptides Derives from the Homodimer Interface of B7-2.

Figure 4A:
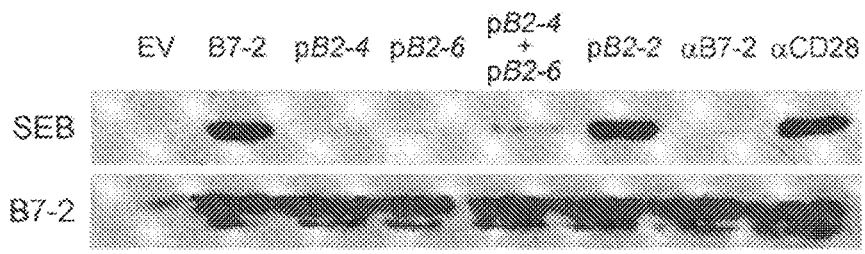

The amino acid sequence of human B7-2 (hB7-2) dimer interface fragment ((1), in which the N-terminal amino acid residue proline (P) is replaced by methionine (M), as denoted by SEQ ID NO: 50), on which the hB7-2 peptide mimetics are denoted. In the extracellular domain of hB7-2, residues in the dimer interface are underlined and residues that contact CTLA4 are in boldface. Peptide sequences are framed.

FIG. 2A-FIG. 2E: Peptide Mimetics of the B7-2 Homodimer Interface are Superantigen Antagonists.

FIG. 2A1-FIG. 2A5 show diagrams of the level of IFN-γ in the presence of the indicated peptides. PBMC were induced with SEB (10 ng/ml), in the absence (open circles in each panel) or presence of 0.1 μg/ml peptide pB2-2 (FIG. 2A1), pB2-3 (FIG. 2A2), pB2-4 (FIG. 2A3), pB2-5 (FIG. 2A4) and pB2-6 (FIG. 2A5) (filled circles), as shown. Secreted IFN-γ was determined (pg/ml×$10^{-2}$) (means±SEM; n=3).

FIG. 2B1-FIG. 2B10 show diagrams of the levels of IL2 in the presence of the indicated peptides, namely pB2-2 (FIG. 2B1), pB2-3 (FIG. 2B2), pB2-4 (FIG. 2B3), pB2-5 (FIG. 2B4) and pB2-6 (FIG. 2B5), and TNF-α in the presence of peptides pB2-2 (FIG. 2B6), pB2-3 (FIG. 2B7), pB2-4 (FIG. 2B8), pB2-5 (FIG. 2B9) and pB2-6 (FIG. 2B10). PBMC were activated by SEB (10 ng/ml) in the absence (open circles) or presence of 0.1 μg/ml of the indicated peptides (filled circles). Secreted IL2 and TNF-α were determined (error bars, SEM; n=3).

FIG. 2C1-FIG. 2C4 show diagrams of the levels of IL-2 (FIG. 2C1), IFN-γ (FIG. 2C2), TNF-α (FIG. 2C3) and IL-10 (FIG. 2C4) in the presence of the below indicated peptides. PBMC were induced with recombinant SEB (0.1 ng/ml), in the absence (open circles) or presence of 0.01 μg/ml pB2-4 (grey filled circles), pB2-6 (black filled circles) or both (black filled squares). Secreted cytokines were determined (means±SEM; n=3).

FIG. 2D1-FIG. 2D4 show diagrams of the levels of IL-2 (FIG. 2D1), IFN-γ (FIG. 2D2), TNF-α (FIG. 2D3) and IL-10 (FIG. 2D4) in the presence of the below-indicated peptides. PBMC were induced with SEB (0.1 ng/ml) alone (open circles) or together with 0.1 g/ml of pB2-7 (filled circles) or 0.01 μg/ml of each pB2-4 and pB2-6 (filled squares). Secreted IL-2, IFN-γ, TNF-α and IL-10 were determined (means±SEM; n=3).

FIG. 2E1-FIG. 2E7 show diagrams of the levels of IL-2 (FIG. 2E1 and FIG. 2E5), IFN-γ (FIG. 2E2 and FIG. 2E6), TNF-α (FIG. 2E3 and FIG. 2E7) and IL-10 (FIG. 2E4) in the presence of the indicated peptides and SMEZ or TSST-1. PBMC were incubated with 0.01 ng/ml SMEZ (FIG. 2E1, FIG. 2E2, FIG. 2E3 and FIG. 2E4) or TSST-1 (FIG. 2E5, FIG. 2E6 and FIG. 2E7) alone (open circles) or together with 0.1 μg/ml of pB2-7 (filled circles) or 0.01 μg/ml of each pB2-4 and pB2-6 (filled squares). Secreted cytokines were determined (error bars, SEM; n=3).

FIG. 3A-FIG. 3F: Peptide Mimetics of the B7-2 Dimer Interface Bind Superantigens and Block Binding of Superantigens to Cell-Surface B7-2 and CD28.

FIG. 3A-FIG. 3B show representative SPR responses diagrams for binding of SEB in twofold increments from 0.78 μM to immobilized pB2-4 (FIG. 3A) and pB2-6 (FIG. 3B).

FIG. 3C-FIG. 3F show representative SPR responses diagrams for binding of TSST-1 in five twofold increments from 0.0625 μM (FIG. 3C and FIG. 3D) and of SMEZ in four twofold increments from 0.0625 μM (FIG. 3E and FIG. 3F) to the immobilized peptides pB2-4 (FIG. 3C and FIG. 3E) or pB2-6 (FIG. 3D and FIG. 3F), using the chips of FIG. 3A-3B.

FIG. 4A-FIG. 4D: The B7-2 Peptide Mimetics Inhibit Binding of SEB to B7-2 or CD28.

Figure 4B:
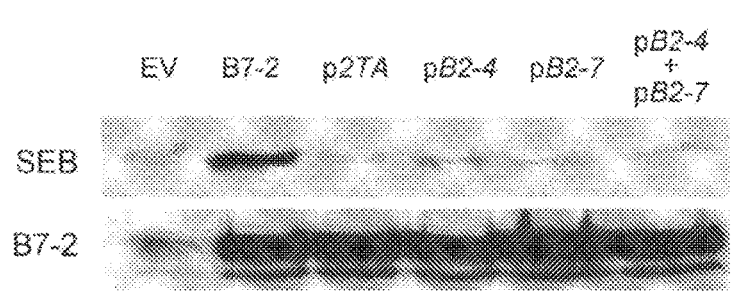
Figure 4C:
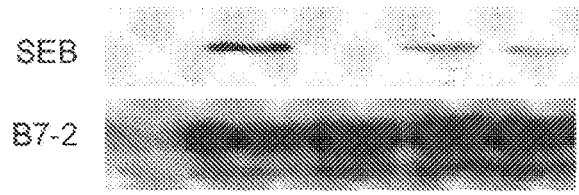

FIG. 4A-FIG. 4C show representative Western blots of inhibition of binding of SEB to cell-surface B7-2 by peptide mimetics of the B7-2 or CD28 homodimer interface. HEK-293T cells were transfected to express B7-2 or with empty vector (EV) and after 36 hours were incubated for 1 hour without addition (B7-2) or as indicated, with 5 μg/ml cB7-2 antibody, αCD28 monoclonal antibody (10) or 10 μg/ml of B7-2 mimetic peptides pB2-2, pB2-4, pB2-6 or pB2-7, or CD28 mimetic peptides p1TA or p2TA (10) before further incubation for 1 hour with 15 μg/ml recombinant SEB. Cells were washed 3 times with cold phosphate-buffered saline before lysis. Western blots of equal amounts of total cell protein (Bradford assay) with 0.1 μg/ml αSEB antibody followed by 0.2 μg/ml horseradish peroxidase-conjugated donkey anti-mouse IgG (top) or with 0.1 μg/ml cB7-2 antibody followed by 0.2 μg/ml horseradish peroxidase-conjugated donkey anti-goat IgG (bottom).

Figure 4D:
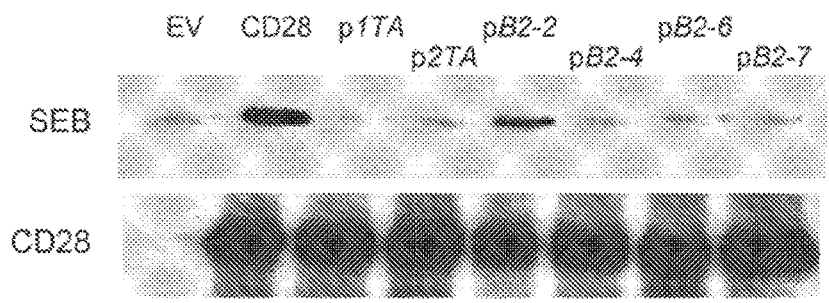

FIG. 4D shows a representative Western blot of inhibition of binding of SEB to cell-surface CD28 by peptide mimetics of the B7-2 or CD28 homodimer interface. HEK-293T cells were transfected to express CD28 (10) or with empty vector before incubation with peptides and SEB as above. Western blots show binding of SEB to CD28 (10) (top) and expression of CD28, assayed with 0.1 μg/ml αCD28 antibody (bottom).

Figures 5A, 5B:
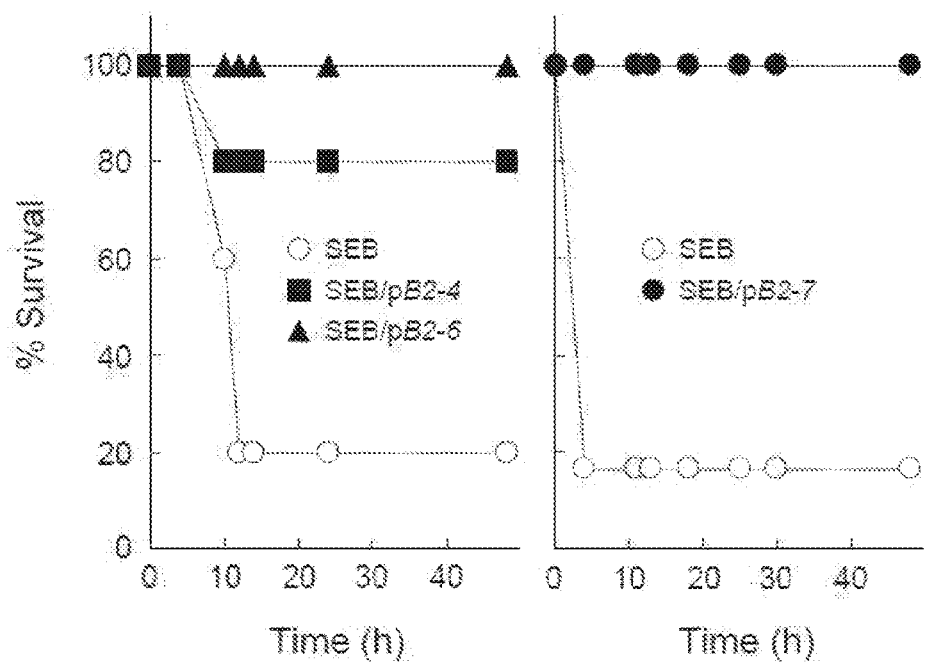

FIG. 5A-FIG. 5B: Peptide Mimetics of the B7-2 Dimer Interface Protect Mice from Lethal SEB Challenge.

FIG. 5A is a diagram showing survival of mice (n=5 per group) injected with SEB (10 μg) alone (open circles) or together with 1 µg of each of the peptide pB2-4 (filled squares) or pB2-6 (filled triangles); p for survival, 0.022.

FIG. 5B is a diagram showing survival of mice (n=6 per group) injected with SEB alone (open circles) or together with 0.2 µg of the peptide pB2-7 (filled circles); p for survival, 0.005. Peptides were administered 30 min before injection of SEB.

Figures 6A, 6B:
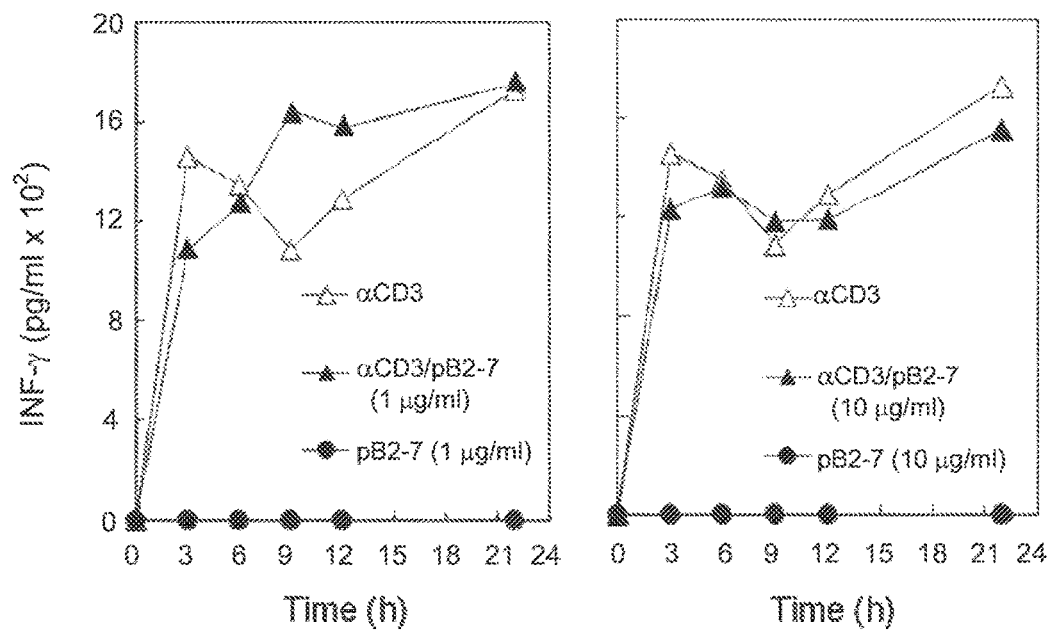

FIG. 6A-FIG. 6B: B7-2 Dimer Interface Mimetic Peptide pB2-7 does not Inhibit Signaling Through the T Cell Receptor.

Human PBMC were induced with αCD3 alone (open triangles), or with αCD3 in the presence of 1 or 10 μg/ml of pB2-7 (filled triangles) (FIG. 6A and FIG. 6B, respectively). Human PBMC were also induced in the presence of 1 or 10 μg/ml of pB2-7 alone (FIG. 6A and FIG. 6B, respectively, filled circles). At the indicated time points, IFN-γ secreted into the culture medium was determined by ELISA.

FIG. 7A-FIG. 7B: B7-2 Dimer Interface Mimetic Peptide pB2-7 Attenuates Signaling Through CD28.

Human PBMC were induced with αCD3/αCD28 alone (open circles), or with αCD3/αCD28 in the presence of 0.01 μg/ml pB2-7 (filled triangles) or 0.001 μg/ml pB2-7 (filled circles). At the indicated time points, IFN-γ (FIG. 7A) and TNF-α (FIG. 7B) secreted into the culture medium were determined by ELISA.

FIG. 8A-FIG. 8B: B7-2 Dimer Interface Mimetic Peptide pB2-4 Attenuates Signaling Through CD28.

Human PBMC were induced with αCD3/αCD28 alone (open circles), or with αCD3/αCD28 in the presence of 0.1 μg/ml of pB2-4 (filled squares) or in the presence of 1 μg/ml of pB2-2 (filled triangles). At the indicated time points, IFN-γ (FIG. 8A) and TNF-α (FIG. 8B) secreted into the culture medium were determined by ELISA.

FIG. 9A-FIG. 9B: B7-2 Dimer Interface Mimetic Peptides Attenuate LPS-Mediated Induction of TNF-α.

Human PBMC were induced with *E. coli* LPS at 25 ng/ml alone (open circles), or with LPS in the presence of 0.1 μg/ml of pB2-4 (filled diamonds), pB2-6 (filled triangles), or both (filled squares) (FIG. 9A), or with *E. coli* LPS at 0.1 μg/ml alone (open circles), or with LPS in the presence of 0.1 μg/ml of pB2-7 (filled circles) (FIG. 9B). At the indicated time points, TNF-α secreted into the culture medium was determined by ELISA.

FIG. 10: B7-2 Dimer Interface Mimetic Peptides Attenuate LPS-Mediated Induction of TNF-α.

Human PBMC were induced with *E. coli* LPS alone (open circles), or with LPS in the presence of 0.01 μg/ml of the peptides pB2-4 (filled triangles), pB2-6 (filled circles), or pB2-7 (filled squares). At the indicated time points, TNF-α secreted into the culture medium was determined by ELISA.

FIG. 11: Peptides Derives from the Homodimer Interface of B7-1.

The amino acid sequence of human B7-1 (hB7-1) dimer interface fragment on which the hB7-1 peptide mimetics are denoted (SEQ ID NO:57). Conserved residues between hB7-2 and hB7-1 are indicated in boldface. Peptide sequences are framed.

FIG. 12: Sequence alignment of segments of the dimer interface of hB7-2 and hB7-1. The sequence alignment shows the amino acid sequence of the peptides pB2-4, pB2-7 and pB2-6, derived from the dimer interface of hB7-2 (SEQ ID NO:58) and the corresponding amino acid sequences of the peptides derived from the dimer interface of hB7-1 (SEQ ID NO:57), namely pB1-4, pB1-7 and pB1-6. Identical amino acids are shown in bold face.

DETAILED DESCRIPTION OF EMBODIMENTS

The presently disclosed subject matter is based on the surprising finding that superantigens bind not only directly to CD28, as previously shown, but also to the CD28 coligand, namely, to B7-2. It is shown herein that binding of B7-2 by the superantigen is essential for superantigen function.

It is also shown herein that superantigens engage B7-2 at its homodimer interface. As evident from the Examples presented below, short peptide mimetics of the B7-2 dimer interface bind diverse superantigens, inhibit superantigen-mediated induction of IL2, IFN-γ and TNF-α in human peripheral blood mononuclear cells, and are effective antagonists in vivo, protecting mice from lethal superantigen challenge.

The B7-2 dimer interface thus serves as a novel therapeutic target for superantigen intoxication. The present findings provide a novel, host-oriented therapeutic approach to the sequelae of superantigen intoxication involving blocking of the indispensible interaction of a superantigen with the dimer interface of B7-2, or with the dimer interface of CD28, through peptides that mimic the dimer interface of B7-2.

Thus far, B7-2 was only considered to function as costimulatory ligand in the immune response. The Examples presented below reveal an unexpected and novel role for B7-2 as a receptor for a class of microbial pathogens, the superantigens. Thus, through direct binding, superantigens make unconventional use not only of CD28 (10), MHC-II and TCR, but also of B7-2.

Short peptide mimetics of the B7-2 homodimer interface are shown herein to be capable of inhibiting the superantigen-mediated induction of IL2, IFN-γ and TNF-α in human peripheral blood mononuclear cells, as demonstrated, for instance, in Example 1. Moreover, these short peptide mimetics of the B7-2 homodimer interface are also shown to be effective SEB antagonists in vivo, protecting mice from lethal toxin challenge, as demonstrated in Example 3 and FIG. 5.

The present disclosure also shows that superantigens engage B7-2 directly at its dimer interface, as implied from the interaction observed for SEB and peptides derived from the dimer interface of B7-2 (FIG. 3A and FIG. 3B).

The dimer interface of B7-2 thus serves as a novel therapeutic target for superantigen intoxication. In particular, for example, peptides D-Ala-pB2-4 and D-Ala-pB2-6 (abutted at both ends by D-Ala, as denoted by SEQ ID NO: 6 and SEQ ID NO: 10, respectively) which are derived from the dimer interface of B7-2 as shown in FIG. 1, blocked the lethality of a specific superantigen, SEB, in mice. As shown in FIG. 5, while only ⅕ control mice survived SEB challenge, survival was demonstrated for ⅘ and 5/5 mice that received D-Ala-pB2-4 and D-Ala-pB2-6, respectively, at the time of SEB administration. Remarkably, the peptides were protective when present in only 2- to 2.4-fold molar excess over SEB. Furthermore, D-Ala-pB2-7 (denoted by SEQ ID NO: 12) which is also derived from the dimer interface of B7-2 as shown in FIG. 1, and spans a region of the dimer interface of B7-2 that overlaps with both the C-terminal region of pB2-4 and the N-terminal region of pB2-6, was shown to be protective against SEB challenge in mice, with 6/6 mice surviving, even when D-Ala-pB2-7 (denoted by SEQ ID NO:12) was present in near-equal molar ratio to SEB (FIG. 5). This high efficacy suggests that the B7-2 dimer interface plays a critical role in mediating the deleterious response to superantigens.

The finding that not only CD28 but also its coligand B7-2 is a direct sensor of a class of microbial pathogens, the superantigens, broadens the scope of pathogen pattern recognition mechanisms.

A direct consequence of the findings presented herein below, is that peptide mimetics of either B7-2 or CD28 dimer interface possess dual antagonist activity, interfering in a reciprocal manner with binding of the superantigen to either receptor. This dual action, documented here, may explain why D-Ala-pB2-7 (having an amino acid sequence denoted by SEQ ID NO:12), a decapeptide mimetic of the B7-2 dimer interface, or p2TA, an octapeptide mimetic of the CD28 dimer interface (10), can effectively protect mice from lethal challenge with SEB, despite that fact that the superantigen, a 238-amino acid protein molecule, interacts with the TCR and MHC-II molecule in addition to binding either B7-2 or CD28.

It was previously reported that the superantigen engages the TCR and MHC-II molecule as well as CD28 with micromolar affinity (10), consistent with the results shown herein below, that B7-2 dimer interface peptides also exhibit micromolar affinity for diverse superantigens (see Table 2). The moderate affinity of a superantigen for its four receptors, including B7-2, can explain why peptides binding with a similarly moderate affinity can disrupt the synapse and thus attenuate the Th1 cytokine response.

It was also previously reported that activation of a Th1 cytokine response by SEB depends upon B7-2 but not B7-1 and is abrogated by a monoclonal antibody directed against B7-2 (10). While these results could be interpreted by a need for costimulation through the interaction of B7-2 with CD28 in the MYPPPY (SEQ ID NO:59) domain, the inventors' findings presented below demonstrate that the superantigen engages B7-2 directly at a distinct domain, the composite dimer interface (1). That this binding is critical for superantigen action is strongly supported by the potent superantigen antagonist activity of B7-2 dimer interface peptides, as shown below, both ex vivo and in vivo.

Although CD28 and B7-2 differ in amino acid sequence and structure at their homodimer interfaces and do not form heterodimers, the superantigen is capable of binding to either of these receptors with an affinity in the micromolar range.

Formation of a quaternary complex between superantigen and MHC-II, TCR and either CD28 or B7-2 is structurally feasible. Within the immunological synapse between antigen-presenting cell and T cell, it is assumed that multiple CD28 and B7-2 molecules engage each other as B7-2/CD28 pairs, thereby creating a network (1). Without being bound by theory, it is thus conceivable that binding of the superantigen to only one receptor within a given pair, rather than to both, may suffice for T cell hyperactivation, as long as both receptors are engaged within the immunological synapse. In the synapse, multiple superantigen molecules must cooperatively engage CD28 and B7-2 to achieve signaling for harmful inflammatory cytokine induction, though not for induction of IL10. These findings modify the current view of superantigen action.

The B7-2 dimer interface has no known role in costimulation and is well separated from the CD28 binding site, as previously reported. Engagement of a superantigen should displace contacts between the B7-2 monomers, which unlike CD28 are not linked through an intermolecular disulfide bond outside the dimer interface and thus require a second-order binding reaction to re-dimerize. The Examples shown below support the interpretation that the superantigen induces a conformational change in B7-2 that activates signaling, likely through the B7-2/CD28 axis. SEB induces vigorous expression of Th1 and Th2 cytokines but only the Th1 response, here defined by induction of the IL2, IFN-γ and TNF-α genes, depends on B7-2 engagement. This mirrors the selective requirement for CD28 in the induction of IL2, IFN-γ and TNF-α genes by superantigens, yet not for the induction of IL4 and IL10 (10). By attenuating this response, the antagonist peptides according to the present disclosure will reduce the synergy between these cytokines, to allow survival.

Thus, based on the inventors' present findings, provided herewith is a novel host-oriented therapeutic approach to the sequelae of superantigen intoxication involving blocking of the indispensible interaction of a superantigen with the dimer interface of B7-2, through peptides that mimic the dimer interface of B7-2.

Therefore, presently disclosed is an isolated and purified peptide comprising at least one amino acid residue of the crystallographic dimer interface within a region of the extracellular domain of human B7-2, said region consisting of the amino acid sequence denoted by SEQ ID NO:13, wherein said crystallographic dimer interface consists of amino acid residues Thr-11, Leu-26, Ser-27, Leu-46, Gly-47, Lys-48, Glu-49, Phe-51, Met-59, Gly-60, Arg-61, Thr-62, Ser-63, Phe-64, Asp-65, Ser-66, Asp-67, Arg-72, His-74 and Asn-75 of SEQ ID NO:13, wherein said isolated and purified peptide further comprises at least 2 additional amino acid residues at its C-terminus and/or N-terminus, wherein said additional amino acid residues are consecutive amino acid residues of SEQ ID NO:13 immediately adjacent to said at least one amino acid residue of said crystallographic dimer interface in SEQ ID NO: 13, wherein said isolated and purified peptide consists of from 3 to about 30 amino acid residues, and functional fragments and derivatives thereof.

Human B7-1 (CD80, Accession number NM_005191) and B7-2 (CD86, Accession number 1185_A) as referred to herein are as described in (1). Unless indicated differently, the terms "B7-1" and "B7-2" refer to human B7-1 (also referred to as "hB7-1") and human B7-2 (also referred to as "hB7-2"), respectively.

As used herein, the term "crystallographic dimer interface" refers to the contact points formed between two identical monomeric protein molecules. Without being bound by theory, these contact points are based on hydrophobic bonding, van der Waals forces, and salt bridges formed between specific amino acid residues comprised in the interface of each of the monomeric protein molecules, thereby forming a dimerization interface. As known in the art and as shown herein below, the specific amino acid residues comprised in the interface of each of the monomeric protein molecules and engaged in forming the dimer interface are not necessarily positioned in the primary amino acid sequence as consecutive amino acid residues. The terms "crystallographic dimer interface of B7-1" and "dimer interface of B7-1" are used herein interchangingly. The terms "crystallographic dimer interface of B7-2" and "dimer interface of B7-2" are used herein interchangingly.

In particular, the presently disclosed subject matter relates to the dimer interface formed between monomeric hB7-2 protein molecules (also referred to as the crystallographic dimer interface of hB7-2). Specific residues that participate in forming the human B7-2 dimer interface were previously reported by Schwartz et al. (1) and are underlined in FIG. 1. The dimer interface of B7-2 is located within a region of the extracellular domain of human B7-2 and thus the presently disclosed subject matter provides isolated and purified peptides consisting of at least one amino acid residue of the dimer interface within a region of the extracellular domain of human B7-2.

Therefore, as detailed above, the presently disclosed subject matter provides an isolated and purified peptide comprising at least one amino acid residue of the dimer interface within a region of the extracellular domain of human B7-2, wherein the region of the extracellular domain of human B7-2 consists of the amino acid sequence denoted by SEQ ID NO:13, namely, the amino acid sequence PLKIQAYFNETADLPCQFANSQNQSL-SELVVFWQDQENLVLNEVYLGKEKFDS VHSKY-MGRTSFDSDSWTLRLHNLQIKDKGLYQCI-IHHKKPTGMIRIHQMNSELS VLA. The following amino acid residues participate in the formation of the dimer interface between monomeric B7-2 protein molecules: Thr-11, Leu-26, Ser-27, Leu-46, Gly-47, Lys-48, Glu-49, Phe-51, Met-59, Gly-60, Arg-61, Thr-62, Ser-63, Phe-64, Asp-65, Ser-66, Asp-67, Arg-72, His-74 and Asn-75 based on the numbering of SEQ ID NO:13.

The isolated and purified peptide according to this disclosure thus consists of at least one of the amino acid residues participating in the formation of the dimer interface between monomeric B7-2 protein molecules recited above, and at least two additional amino acid residues at each of its C-terminus and/or N-terminus, wherein said additional amino acid residues are consecutive amino acid residues of SEQ ID NO: 13 immediately adjacent to said at least one amino acid residue of said dimer interface in SEQ ID NO: 13, wherein said isolated and purified peptide consists of from 3 to about 30 amino acid residues, and functional fragments and derivatives thereof.

Thus, in the above and other embodiments, the length of the isolated and purified peptide according to the present disclosure is from 3 to about 30 amino acid residues. In some embodiments the length of the isolated and purified peptide according to the present disclosure is from 3 to 29, from 3 to 28, from 3 to 27, from 3 to 26, from 3 to 25, from 3 to 24, from 3 to 23, from 3 to 22, from 3 to 21, from 3 to 20, from 3 to 19, from 3 to 18, from 3 to 17, from 3 to 16, from 3 to 15, from 3 to 14, from 3 to 13, from 3 to 12, from 3 to 11, from 3 to 10, from 3 to 9, from 3 to 8, from 3 to 7, from 3 to 6, from 3 to 5, from 3 to 4 amino acid residues. Specific peptides consist of 3, 4, 5, 6, 7, 8, 9, 10, 11, 12, 13 and 14 amino acid residues. Derivatives of the peptides according to the present invention wherein the peptide is extended by one or more amino acid residues can be longer, as described below In the above and other embodiments of the presently disclosed subject matter the isolated and purified peptide according to the invention comprises said at least one amino acid residue of said crystallographic dimer interface and from 2 to about 8, for example 2 to 8, 3 to 8, 4 to 8, 5 to 8, 6 to 8 or 7 to 8, more specifically 2, 3, 4, 5, 6, 7 or 8 said additional amino acid residues at its C-terminus and/or N-terminus, and functional fragments and derivatives thereof.

The term "consecutive amino acid residues of an amino acid sequence" as herein defined refers to amino acid residues that correspond to amino acid residues of a reference amino acid sequence (namely SEQ ID NO: 13 or SEQ ID NO: 14) in positions that are immediately adjacent to said at least one amino acid residue of said dimer interface and which are contiguous (located one after the other) in the reference amino acid sequence.

By the term "immediately adjacent to an amino acid in an amino acid sequence" as used herein is meant an amino acid residue next to, or immediately preceding, or immediately following this amino acid residue in the corresponding position/s in the reference amino acid residues.

In some embodiments, the isolated and purified peptide of the presently disclosed subject matter, consists of an amino acid sequence selected from the amino acid sequences denoted by SEQ ID NO:5 (EKFDSVHSKYM, also designated peptide pB2-4), SEQ ID NO:9 (DSDSWTLR also designated peptide pB2-6), SEQ ID NO:11 (MGRTSFDSDS, also designated pB2-7), SEQ ID NO:18 (FNETADLP), SEQ ID NO:20 (NQSLSELV), SEQ ID NO:22 (YLGKEKFD), SEQ ID NO:24 (TLRLHNLQ), SEQ ID NO:26 (YMGRTSFDSD), and SEQ ID NO:44 (LGKEKFDSVHSKYMGRTSFDSDSWTLRLHN), and functional fragments and derivatives thereof.

In other embodiments the isolated and purified peptide according to the presently disclosed subject matter consists of an amino acid sequence selected from the amino acid sequences denoted by SEQ ID NO:11 (MGRTSFDSDS, also designated pB2-7), SEQ ID NO:5 (EKFDSVHSKYM, also designated peptide pB2-4) and SEQ ID NO:9 (DSDSWTLR also designated peptide pB2-6) and functional fragments and derivatives thereof.

In specific embodiments the isolated and purified peptide according to the presently disclosed subject matter is of the amino acid sequence denoted by SEQ ID NO:5 (EKFDSVHSKYM, also designated peptide pB2-4).

In other specific embodiments the isolated and purified peptide according to the presently disclosed subject matter is of the amino acid sequence denoted by SEQ ID NO:9 (DSDSWTLR also designated peptide pB2-6).

In further specific embodiments the isolated and purified peptide according to the presently disclosed subject matter is of the amino acid sequence denoted by SEQ ID NO:11 (MGRTSFDSDS, also designated pB2-7).

It is noteworthy that only isolated and purified peptides comprising at least one amino acid residue of the dimer interface of the extracellular domain of human B7-2, as defined above, were shown to actively inhibit cytokine induction. As shown for example in FIG. 2A, the peptides D-Ala-pB2-2, D-Ala-pB2-3 and D-Ala-pB2-5 (having amino acid sequences as denoted in Table 3 below) which do not comprise any amino acid residue of said dimer interface, failed to inhibit the SEB-mediated induction of IFN-γ in human PBMC, whereas D-Ala-pB2-4 and D-Ala-pB2-6 exhibited very strong inhibitory activity. Likewise, as shown in FIG. 2B, D-Ala-pB2-4 and D-Ala-pB2-6, but not the other three peptides D-Ala-pB2-2, D-Ala-pB2-3 and D-Ala-pB2-5 peptides, inhibited the induction of IL2 and TNF-α by SEB.

According to another aspect, the presently disclosed subject matter provides an isolated and purified peptide comprising at least one amino acid residue of the crystallographic dimer interface within a region of the extracellular domain of human B7-1, said region consisting of the amino acid sequence denoted by SEQ ID NO:14, wherein said crystallographic dimer interface consists of amino acid residues Val-15, Leu-29, Ala-30, Ser-48, Gly-49, Asp-50, Met-51, Lys-58, Asn-59, Arg-60, Thr-61, Ile-62, Phe-63, Asp-64, Ile-65, Thr-66, Val-72, Leu-74 and Ala-75 of SEQ ID NO: 14, wherein said isolated and purified peptide further comprises at least 2 additional amino acid residues at its C-terminus and/or N-terminus, wherein said additional amino acid residues are consecutive amino acid residues of SEQ ID NO: 14 immediately adjacent to said at least one amino acid residue of said crystallographic dimer interface in SEQ ID NO:14, wherein said isolated and purified peptide consists of from 3 to about 30 amino acid residues, and functional fragments and derivatives thereof.

Thus, as indicated above, the presently disclosed subject matter also relates to the dimer interface formed between monomeric protein molecules of hB7-1, which is homologous to hB7-2.

B7-1 is homologous to B7-2, both acting as costimulatory ligands expressed on the surface of antigen presenting cells (APCs). Binding of these molecules to the T cell costimulatory receptors, CD28 and CTLA-4, is essential for the activation and regulation of T cell immunity. Despite strong structural similarities, B7-1 and B7-2 exhibit different biochemical features, and their binding to the costimulatory receptors results in distinct T cell functional outcomes.

Specific residues that participate in forming the human B7-1 dimer interface were also described in Schwartz, J. C. et al. (1 and references therein). In addition, some of the specific residues participating in forming the human B7-1 dimer interface are underlined in FIG. 12.

The dimer interface of B7-1 is located within a region of the extracellular domain of human B7-1 and thus the present invention provides an isolated and purified peptide consisting of at least one amino acid residue of the dimer interface within a region of the extracellular domain of human B7-1.

Therefore the presently disclosed subject matter relates to an isolated and purified peptide comprising at least one amino acid residue of the dimer interface within a region of the extracellular domain of human B7-1, said region consisting of the amino acid sequence denoted by SEQ ID NO: 14, namely, the amino acid sequence:

FCSGVIHVTKEVKEVATLSCGHNVSVEELAQTRIYWQKEKKMVLTMMSGDM

NIWPEYKNRTIFDITNNLSIVILALRPSDEGTYECVVLKYEKDAFKREHLA

EVTLSVKA.

The following amino acid residues participate in the formation of the dimer interface between monomeric B7-1 protein molecules: Val-15, Leu-29, Ala-30, Ser-48, Gly-49, Asp-50, Met-51, Lys-58, Asn-59, Arg-60, Thr-61, Ile-62, Phe-63, Asp-64, Ile-65, Thr-66, Val-72, Leu-74 and Ala-75 based on the numbering of SEQ ID NO: 14.

The B7-1 related isolated and purified peptide according to the present disclosure thus consists of at least one of the amino acid residues participate in the formation of the dimer interface between monomeric B7-1 protein molecules recited above and at least 2 additional amino acid residues at each of its C-terminus and/or N-terminus, wherein said additional amino acid residues are consecutive amino acid residues of SEQ ID NO:14 immediately adjacent to said at least one amino acid residue of said dimer interface in SEQ ID NO: 14, wherein said isolated and purified peptide consists of from 3 to about 30 amino acid residues, and functional fragments and derivatives thereof.

In the above and other embodiments, the B7-1 related isolated and purified peptide according to the present disclosure thus consists of at least one of the amino acid residues participate in the formation of the dimer interface between monomeric B7-1 protein molecules recited above and from 2 to about 8, consecutive amino acid residues immediately adjacent thereto in SEQ ID NO:14, at each of its C-terminus and/or N-terminus, and functional derivatives thereof.

In other words, in some embodiments the isolated and purified peptide according to the invention comprises said at least one amino acid residue of the crystallographic dimer interface within a region of the extracellular domain of human B7-1, said region consisting of the amino acid sequence denoted by SEQ ID NO: 14, and from 2 to about 8, for example 2 to 8, 3 to 8, 4 to 8, 5 to 8, 6 to 8 or 7 to 8, more specifically 2, 3, 4, 5, 6, 7 or 8 additional amino acid residues at its C-terminus and/or N-terminus, wherein said additional amino acid residues are consecutive amino acid residues of SEQ ID NO:14 located immediately adjacent to said at least one amino acid residue of said crystallographic dimer interface in SEQ ID NO:14, and functional fragments and derivatives thereof.

In some embodiments, the B7-1 related isolated and purified peptide according to the invention consists of an isolated and purified peptide consisting of an amino acid sequence selected from the amino acid sequences denoted by SEQ ID NO:28 (VKEVATLS), SEQ ID NO:30 (VEELAQTR), SEQ ID NO:32 (MSGDMNIW), SEQ ID NO:34 (SIVILALR), SEQ ID NO:36 (YKNRTIFDIT), SEQ ID NO:38 (MNIWPEYK, denoted pB1-4), SEQ ID NO:40 (KNRTIFDITN, denoted pB1-7) and SEQ ID NO:42 (DITNNLSIV, denoted pB1-6), SEQ ID NO:46 (SGDMNIWPEYKNRTIFDITNNLSIVILA) and SEQ ID NO:48 (YKNRTIFD, denoted pB1-8) and functional derivatives thereof.

In further embodiments, the B7-1 related isolated and purified peptide according to the invention consists of an isolated and purified peptide consisting of an amino acid sequence selected from the amino acid sequences denoted by SEQ ID NO:38 (MNIWPEYK, denoted pB1-4), SEQ ID NO:40 (KNRTIFDITN, denoted pB1-7), SEQ ID NO:42 (DITNNLSIV, denoted pB1-6), SEQ ID NO:46 (SGDMNIWPEYKNRTIFDITNNLSIVILA) and SEQ ID NO:48 (YKNRTIFD, denoted pB1-8) and functional derivatives thereof.

As indicated above, the presently disclosed subject matter provides isolated and purified peptides consisting of at least one amino acid residue of the dimer interface within a region of the extracellular domain of human B7-2, or an isolated and purified peptide consisting of at least one amino acid residue of the dimer interface within a region of the extracellular domain of the human B7-1, and functional derivatives thereof. The terms "peptide", "oligopeptide" or "polypeptide" as used herein refer to amino acid residues, connected by peptide bonds.

More specifically, "amino acid sequence" or "peptide sequence" is the order in which amino acid residues, connected by peptide bonds, lie in the chain in peptides and proteins. The sequence is generally reported from the N-terminal end containing free amino group to the C-terminal end containing amide.

The term "amino acids" as used herein refers to naturally occurring and synthetic amino acids, as well as amino acid analogs and amino acid mimetics that can function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

It should be noted that the polypeptides according to the invention can be produced synthetically, or by recombinant DNA technology. Methods for producing polypeptides peptides are well known in the art.

It should be noted that in addition to any of the peptides, further encompassed in the presently disclosed subject matter are any functional fragments thereof. "functional fragments" within the scope of these disclosure are 3 to about 20 amino acid residues fragments of the disclosed novel peptides, of which at least one amino acid residue is an amino acid residues of the dimer interface of human B7-2 (Thr-11, Leu-26, Ser-27, Leu-46, Gly-47, Lys-48, Glu-49, Phe-51, Met-59, Gly-60, Arg-61, Thr-62, Ser-63, Phe-64, Asp-65, Ser-66, Asp-67, Arg-72, His-74 and Asn-75 of SEQ ID NO:13) for fragments of the present human B7-2-derived peptides or at least one amino acid residue of the dimer interface of human B7-1 (Val-15, Leu-29, Ala-30, Ser-48, Gly-49, Asp-50, Met-51, Lys-58, Asn-59, Arg-60, Thr-61, Ile-62, Phe-63, Asp-64, Ile-65, Thr-66, Val-72, Leu-74 and Ala-75 of SEQ ID NO:14), for fragments of the present human B7-1-derived peptides.

It should be noted that in addition to any of the peptides of the invention, the invention further encompasses any functional derivatives thereof. The term "functional derivative" of "derivative" is used to define amino acid sequences (peptides), with any insertions, deletions, substitutions and modifications to the amino acid sequences (peptides) that do not alter the activity of the original polypeptides. By the term "derivative" it is also referred to homologues, variants and analogues thereof, as well as covalent modifications of a polypeptides made according to the present invention.

The terms "fragments", "derivatives" and "functional derivatives" as used herein mean any of the peptides of the invention, specifically hB-1 mimetic peptides or hB-2 mimetic peptides as defined herein, with any insertions, deletions, substitutions and modifications to the peptide that do not interfere with their ability to therapeutically affect bacterial and other infections, as well as inflammations associated therewith, as described herein.

In some embodiments, derivatives refer to peptides, which differ from the peptides specifically defined in the presently disclosed subject matter by insertions or deletions of amino acid residues. It should be appreciated that by the terms "insertions" or "deletions", as used herein it is meant any addition or deletion, respectively, of amino acid residues to the polypeptides used by the invention, of between 1 to 50 amino acid residues, between 1 to 1 amino acid residues, and specifically, between 1 to 10 amino acid residues. More particularly, insertions or deletions may be of any one of 1, 2, 3, 4, 5, 6, 7, 8, 9, or 10 amino acids. It should be noted that the insertions or deletions encompassed by the invention may occure in any position of the modified peptide, as well as in the N- and/or C-terminus thereof.

By way of a non-limiting example, the term "modifications" as used herein refers to derivatives of peptides according to the presently disclosed subject matter that are positively charged, negatively charged or neutral. In addition, the peptides of the invention may be in the form of a dimer, a multimer or in a constrained conformation, which can be attained by internal bridges, short-range cyclizations, extension or other chemical modifications.

Further, the peptides may be extended at the N- and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A specific synthetic amino acid residue with which the peptide may be extended at its N-terminus and/or C-terminus is D-alanine.

An additional example for such an extension may be provided by peptides extended both at the N- and/or C-terminus thereof with a cysteine residue. In some embodiments, the presently disclosed peptides can be coupled through their N-terminus to a lauryl-cysteine (LC) residue and/or through their C-terminus to a cysteine (C) residue. Naturally, such an extension may lead to a constrained conformation due to Cys-Cys cyclization resulting from the formation of a disulfide bond.

Another example may be the incorporation of an N-terminal lysyl-palmitoyl tail, the lysine serving as linker and the palmitic acid as a hydrophobic anchor. In addition, the peptides may be extended by aromatic amino acid residue/s, which may be naturally occurring or synthetic amino acid residue/s, for example a specific aromatic amino acid residue may be tryptophan. The peptides may be extended at the N- and/or C-terminus thereof with various identical or different organic moieties which are not naturally occurring or synthetic amino acids. As an example for such extension, the peptide may be extended at the N- and/or C-terminus thereof with an N-acetyl group.

For every single peptide sequence used in the presently disclosed subject matter and disclosed herein, also included is the corresponding retro-inverse sequence wherein the direction of the peptide chain has been inverted and wherein all the amino acids belong to the D-series.

The presently disclosed subject matter also encompasses any substitutions of the peptides disclosed herein. Conservative substitution tables providing functionally similar amino acids are well known in the art. Such conservatively modified variants are in addition to and do not exclude polymorphic variants, interspecies homologues, and alleles and analogous peptides of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

More specifically, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R)

and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

The presently disclosed subject matter also encompasses any homologues, variants and analogues of the peptides disclosed herein (either the peptides derived from the dimer interface of the human B7-2 (also referred to herein as "hB7-2 mimetic peptides") or the peptides derives from the dimer interface of the human B7-1 (also referred to herein as "hB7-1 mimetic peptides") specifically defined by their amino acid sequence according to the presently disclosed subject matter.

In some embodiments, the functional derivative of the isolated and purified peptide according to the presently disclosed subject matter is any one of:

i. said B7-2 mimetic peptide that is extended at the N terminus and/or the C terminus thereof by 1 to 4 consecutive amino acid residues present in immediately adjacent corresponding positions of the amino acid sequence denoted by SEQ ID NO: 13;

ii. said B7-2 mimetic peptide that is extended at the N terminus and/or the C terminus thereof:
 (a) by cysteine or by lauryl cysteine;
 (b) by an organic moiety that is not naturally occurring or by a synthetic amino acid residue;
 (c) by N-acetyl or lysyl-palmitoyl residue;
 (d) by hydrophobic amino acid residue(s) which may be naturally occurring or synthetic amino acid residues; or iii. a dimer or multimer of any of the peptides of (i) and (ii);

iv. a constrained conformation of said B7-2 mimetic peptide;

v. any of said B7-2 mimetic peptides and their derivatives as defined in (i) to (iv), that is modified by at least one synthetic mutation selected from insertion, deletion, substitution, provided that the modified peptide comprises at least one amino acid residue of the said dimer interface;

wherein said derivative consists of from 3 to about 40 amino acid residues.

In some other embodiments, the functional derivative of the isolated and purified peptide according to the presently disclosed subject matter is any one of:

i. said B7-1 mimetic peptide that is extended at the N terminus and/or the C terminus thereof by 1 to 4 consecutive amino acid residues present in immediately adjacent corresponding positions of the amino acid sequence denoted by SEQ ID NO: 14;

ii. said B7-1 mimetic peptide that is extended at the N terminus and/or the C terminus thereof:
 (a) by cysteine or by lauryl cysteine;
 (b) by an organic moiety that is not naturally occurring or by a synthetic amino acid residue;
 (c) by N-acetyl or lysyl-palmitoyl residue;
 (d) by hydrophobic amino acid residue(s) which may be naturally occurring or synthetic amino acid residues; or iii. a dimer or multimer of any of the peptides of (i) and (ii);

iv. a constrained conformation of said B7-1 mimetic peptide;

v. any of said B7-1 mimetic peptides and their derivatives as defined in (i) to (iv), that is modified by at least one synthetic mutation selected from insertion, deletion, substitution, provided that the modified peptide comprises at least one amino acid residue of the said dimer interface;

wherein said derivative consists of from 3 to about 40 amino acid residues.

In some specific embodiments the isolated peptide according to presently disclosed subject matter is extended at its N terminus and/or at its C terminus by a D-Ala amino acid residue.

In further embodiments the isolated peptide according to the presently disclosed subject matter is extended at its N terminus and/or at its C terminus by the amino acid D-Ala and is selected from the group consisting of SEQ ID NO:6, SEQ ID NO:10, SEQ ID NO:12, SEQ ID NO:19, SEQ ID NO:21, SEQ ID NO:23, SEQ ID NO:25, SEQ ID NO:27 and SEQ ID NO:45 for peptides derived from the dimer interface of hB7-2 and from the group consisting of SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:47 and SEQ ID NO: 49 for peptides derived from the dimer interface of hB7-1.

In some embodiments the isolated peptide as herein defined is any one of a peptide consisting of the amino acid sequence (D-A)EKFDSVHSKYM(D-A) as denoted by SEQ ID NO: 6 (also designated herein as peptide D-Ala-pB2-4), a peptide consisting of the amino acid sequence (D-A) DSDSWTLR(D-A) as denoted by SEQ ID NO: 10 (also designated herein as peptide D-Ala-pB2-6) and a peptide consisting of the amino acid sequence (D-A) MGRTSFDSDS(D-A) as denoted by SEQ ID NO: 12 (also designated herein as peptide D-Ala-pB2-7).

In specific embodiments the isolated peptide as herein defined is of the amino acid sequence (D-A)EKFDSVHS-KYM(D-A) as denoted by SEQ ID NO: 6 (also designated herein as peptide D-Ala-pB2-4).

In other specific embodiments the isolated peptide as herein defined is of the amino acid sequence (D-A)DSD-SWTLR(D-A) as denoted by SEQ ID NO: 10 (also designated herein as peptide D-Ala-pB2-6).

In further specific embodiments the isolated peptide as herein defined is of the amino acid sequence (D-A) MGRTSFDSDS(D-A) as denoted by SEQ ID NO: 12 (also designated herein as peptide D-Ala-pB2-7).

The D-Ala residues were added to the hB7-2 mimetic peptides of the present disclosure at both their C- and N-termini, solely for conferring greater protease resistance in biological assays. The terms "D-Ala-" and "(D-A)" are used herein interchangeably. In further specific embodiments the isolated peptide as herein defined is any one of a peptide consisting of the amino acid sequence (D-A) MNIWPEYK(D-A) as denoted by SEQ ID NO: 39 (also designated D-Ala-pB1-4), a peptide consisting of the amino acid sequence (D-A)KNRTIFDITN(D-A) as denoted by SEQ ID NO:41 (also designated D-Ala-pB1-7), a peptide consisting of the amino acid sequence (D-Ala)DITNNLSIV (D-Ala) as denoted by SEQ ID NO:43 (also designated D-Ala-pB1-6), and a peptide consisting of the amino acid sequence (D-Ala)YKNRTIFD(D-Ala) denoted by SEQ ID NO:49 (also designated D-Ala-pB1-8).

The D-Ala residues are added to the hB7-1 mimetic peptides of the present disclosure at both their C- and N-termini, solely for conferring greater protease resistance in biological assays.

The isolated and purified peptides according to all aspects and embodiments of the present disclosure, and their functional fragments and derivatives, are synthetic, non-naturally occurring, man-made peptides. The peptides are synthetic, non-naturally occurring, man-made peptides also when any or all of their amino acids are naturally occurring per se.

The terms "synthetic peptide/s", "non-naturally occurring peptide/s" and "man-made peptide/s" as used herein are to be taken to mean peptides that cannot be found in nature as such at their specific length and amino acid sequence.

As used herein, the term "isolated", in the context of the presently disclosed subject matter, means amino acid sequences which may have partial or complete homology to naturally occurring peptides, polypeptides are proteins, but are of limited lengths, and differ, at least in length, from such naturally occurring sequences. For example, isolated peptides according to the presently disclosed subject matter can be specific, defined fragments of a region of the extracellular domain of human B7-2 or human B7-1, of shorter length and are not expected to be found as such at their natural milieu. Isolated peptides are generally prepared synthetically, by chemical synthesis, chemically or enzymatically, by cleaving a naturally occurring sequence, or sometimes by recombinant techniques.

As such, "isolated" does not necessarily reflect the extent to which the amino acid molecules have been purified. However, it will be understood that such molecules that have been purified to some degree are "isolated". If said molecules do not exist in a natural milieu, i.e. they do not exist in nature, the molecule is "isolated" regardless of where it is present.

Furthermore, the term "purified" or "substantially purified", when applied to peptides, denotes that the peptides are essentially free of other cellular components with which they are associated in the natural state. Rather, the peptides are in a homogeneous state, although they can be either dry or in solution. Purity and homogeneity are typically determined using analytical chemistry techniques such as polyacrylamide gel electrophoresis or high performance liquid chromatography. A peptide molecule which is the predominant species present in a preparation is purified or substantially purified.

The present disclosure further provides a pharmaceutical composition comprising as an active ingredient at least one isolated and purified peptide as defined herein optionally further comprising a pharmaceutically acceptable carrier, diluent, adjuvant and/or excipient.

In some embodiments the pharmaceutical composition as herein defined comprises as an active ingredient at least one, or at least two, or at least three or more isolated and purified peptides as herein defined, optionally further comprising a pharmaceutically acceptable carrier, diluent, adjuvant and/or excipient.

As shown below in Example 3 and FIGS. 5A and 5B, mice challenged with SEB, that were administered with peptides D-Ala-pB2-4, D-Ala-pB2-6 and D-Ala-pB2-7 30 minutes before SEB challenge, survived SEB challenge (FIG. 5A). Notably, the peptide D-Ala-pB2-7 protected when present in only 2- to 3-fold molar excess over SEB (FIG. 5B). This high efficacy supports a critical role for the B7-2 dimer interface in mediating the deleterious response to superantigens.

Therefore in another one of its aspects the present disclosure provides the disclosed peptides and pharmaceutical compositions comprising them herein defined, for eliciting protective immunity against at least one of sepsis, toxic shock, septic shock, severe sepsis, incapacitation and resulting death, that are induced by a bacterial pathogen, a mixture of bacterial pathogens and/or a toxic bacterial component.

The term "eliciting protective immunity" as herein defined means protecting animals infected with lethal pathogenic bacteria and/or lethal toxic bacterial components against the toxic shock induced, including septic shock, sepsis and/or severe sepsis, incapacitation and resulting death from any thereof, thereby leading to rescue and survival of infected/challenged animal from the induced toxic shock.

Without being bound by theory, it is also suggested that a result of treatment and rescue of animals infected with lethal pathogenic bacteria and/or lethal toxic bacterial components may be the conferring of long-term protective immunity against toxic shock, septic shock, severe sepsis, incapacitation and resulting death, that are induced by lethal bacterial pathogen/s and/or toxic bacterial component/s and the infected/challenged animals not only survive immediate shock, but acquire protective immunity against any further toxin challenges. This is because by blocking the ability of the toxin to induce a cellular immune response leading to toxic shock, the antagonist peptides of the present disclosure may allow the superantigen to induce an immune response directed against itself.

By another one of its aspects the present disclosure provides a peptide as herein defined for use in a method for eliciting in a human subject in need protective immunity against at least one of sepsis, toxic shock, septic shock, severe sepsis, incapacitation and resulting death, that are induced by a bacterial pathogen, a mixture of bacterial pathogens and/or a toxic bacterial component.

By still another one of its aspects the present disclosure provides a pharmaceutical composition as herein defined for use in a method for eliciting in a human subject in need protective immunity against at least one of sepsis, toxic shock, septic shock, severe sepsis, incapacitation and resulting death, that are induced by a bacterial pathogen, a mixture of bacterial pathogens and/or a toxic bacterial component.

The pharmaceutical compositions of the presently disclosed subject matter generally comprise a buffering agent, an agent which adjusts the osmolarity thereof, and optionally, one or more pharmaceutically acceptable carriers, diluent, adjuvant and/or excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The carrier, diluent, adjuvant and/or excipient do not interfere with the activity of the peptide.

Salts and esters of the presently disclosed peptides are also encompassed by the presently disclosed subject matter. The term "salts" as herein defined refers to a pharmaceutically acceptable salt, e.g., non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the active compounds used herein with a suitable organic or inorganic acid. Specific acid addition salts may be hydrochloride, acetate, maleate, malate, tartrate, salicylate, citrate or malonate salts, and solvates, e.g. hydrates thereof.

The term "ester" as herein defined refers to a pharmaceutically acceptable ester, e.g. esters which retain, upon hydrolysis of the ester bond, the biological effectiveness and properties of the carboxylic acid or alcohol and are not biologically or otherwise undesirable. Generally, ester formation can be accomplished via conventional synthetic techniques.

In specific embodiments, said pharmaceutical composition can be in sustained- or controlled-release form, or in a combined sustained/controlled-release and immediate release forms.

In the above and other embodiments of the disclosed subject matter, the peptide may be comprised in a pharmaceutical unit dosage form, said dosage form optionally further comprising at least one of physiologically compatible additives, carriers, peptide stabilizers, diluents and excipients. For example, said dosage form may optionally further comprise protease inhibitors.

In the above and other aspects and embodiments of the disclosed subject matter, the pharmaceutical composition can be used for the treatment of at least one of a bacterial infection and acute inflammation associated therewith in a human subject.

Bacterial infections in human are generally induced by at least one of Gram-positive bacteria, Gram-negative bacteria and toxic bacterial components. Where infection is with more than one bacterium, it may be referred to as a polymicrobial infection, as defined below.

Thus in the above and other embodiments of the disclosed subject matter, the pharmaceutical composition can be used for the treatment of at least one of bacterial infection and acute inflammation associated therewith, induced by at least one of Gram-positive bacteria, Gram-negative bacteria, and at least one toxic bacterial component.

In specific embodiments the peptide or the pharmaceutical composition comprising as an active ingredient at least one isolated and purified peptide as herein defined is for use in a method of treating at least one of bacterial infection and acute inflammation associated therewith in a human subject in need, wherein said pharmaceutical composition optionally further comprises a pharmaceutically acceptable carrier, diluent, adjuvant and/or excipient.

Gram-negative bacteria as herein defined and as known in the art are bacteria that do not retain crystal violet dye in the Gram staining protocol, due to the existence of an outer membrane preventing the penetration of the stain. In contrast, Gram positive bacteria will retain the crystal violet dye when washed in a decolorizing solution. The pathogenic capability of Gram-negative bacteria is often associated with certain components of Gram-negative cell envelope, in particular, the lipopolysaccharides (LPS) layer. In humans, LPS triggers an innate immune response characterized by cytokine production and immune system activation, which is often associated with inflammation.

Thus in the above and other embodiments of the disclosed subject matter, the Gram-negative bacteria can be, but are not limited to, any one of proteobacteria, *Escherichia coli*, *Salmonella*, *Shigella*, *Enterobacteriaceae*, *Pseudomonas*, *Moraxella*, *Helicobacter*, *Bdellovibrio*, *Stenotrophomonas*, acetic acid bacteria, *Legionella*, alpha-proteobacteria, *Wolbachia*, Gram-negative cocci, *Neisseria* species, *Neisseria gonorrhoeae*, *Neisseria meningitidis*, *Moraxella catarrhalis*, Gram-negative bacilli, *Hemophilus influenzae*, *Klebsiella pneumoniae*, *Legionella pneumophila*, *Pseudomonas aeruginosa*, *Proteus mirabilis*, *Enterobacter cloacae*, *Serratia marcescens*, *Helicobacter pylori*, *Salmonella enteritidis*, *Salmonella typhi*, *Acinetobacter baumannii*, *Francisella tularemia*, *Vibrio*, *vulnificus*, *cholerae*, *fluvialis*, *parahemolyticus*, *alginolyticus*, *Photobacter damsela*, *Aeromonas hydrophila*, *Clostridium perfringens*, *Clostridium histolyticum*, *Porphyromonas/prevotella* sp. *Prevotella Intermedia*, *Prevotella Buccae*, *Prevotella* sp., *Bacteroides uniformis* and NDM-1 bacterial strains.

Gram-positive bacteria as known in the art are herein defined as bacteria that are stained dark blue or violet by Gram staining, in contrast to Gram-negative bacteria, as recited above. As a non-limiting example, Group A streptococci (GAS) are Gram positive bacteria responsible for a wide range of both invasive and non-invasive infections. GAS produce a range of superantigenic toxins which are believed to be important in the pathogenesis of invasive streptococcal infections such as streptococcal toxic shock syndrome.

Thus in the above and other embodiments of the disclosed subject matter, the Gram-positive bacteria are selected from the group consisting of Group A *streptococcus*, *S. pyogenes*, *S. pneumonia*, Group B strep, *Enterococcus faecalis*, Group D *streptococcus*, Group G *streptococcus*, *Streptococcus viridans*, *Streptococcus milleri*, *Propionibacterium* sp., *Enterococcus faecium*, *Peptostreptococcus* sp., *Streptococcus Microaerophilic*, *Lactobacillus* sp., *Staphylococcus Epidermis* and *Staphylococcus aureus*.

The bacterium *Staphylococcus aureus* (also referred to as *S. aureus* or *Staph. aureus*) is a facultative anaerobic Gram-positive coccal bacterium, which is frequently found in the human respiratory tract and on the skin. Although *S. aureus* is not always pathogenic, it is a common cause of skin infections (e.g. boils), respiratory disease (e.g. sinusitis), and food poisoning. Disease-associated strains often promote infections by producing potent protein toxins. The emergence of antibiotic-resistant forms of pathogenic *S. aureus* is a worldwide problem in clinical medicine.

*Streptococcus pyogenes* is a spherical, Gram-positive bacterium that is the cause of group A streptococcal infections. *S. pyogenes* displays streptococcal group A antigen on its cell wall. It is estimated that there are more than 700 million infections world-wide each year and over 650,000 cases of severe, invasive infections that have a mortality rate of 25%. Early recognition and treatment are critical and failure in diagnosis may result in sepsis and death.

The term "polymicrobial infection" as used herein is to be taken to mean an infection consisting of/induced by several species of bacteria. The bacterial infection may be caused by a mixture of Gram-positive bacteria, by a mixture of Gram-negative bacteria or by a mixture of both Gram-positive and Gram-negative bacteria. A polymicrobial infection can also be caused by a mixture of aerobic bacteria, anaerobic bacteria or both.

Therefore, in the above and other embodiments of the disclosed subject matter said polymicrobial infection is induced by Gram-positive bacteria, Gram-negative bacteria, or a combination thereof.

Bacterial toxins and other toxic bacterial components are well known in the art. Bacteria generate toxins which can be classified as either exotoxins or endotoxins. While exotoxins are generated and actively secreted, endotoxins remain part of the bacteria. The response of the host to an endotoxin can involve severe inflammation. While generally the inflammation process is usually clinically considered beneficial to the infected host, when the reaction is severe, it may lead to sepsis. In particular, the terms "superantigen toxin" or "superantigen" (also referred to as "SAgs") as used herein refers to a class of bacterial pyrogenic exotoxins that cause non-specific activation of T-cells resulting in polyclonal T cell activation and massive cytokine release.

Staphylococcal enterotoxin B (SEB) is an enterotoxin produced by the bacterium *Staphylococcus aureus*, which is a Gram-positive coccal bacterium. It is a common cause of food poisoning, with severe diarrhea, nausea and intestinal cramping often starting within a few hours of ingestion. Being quite stable, the toxin may remain active even after the contaminating bacteria are killed. It can withstand boiling at 100° C. for a few minutes. SEB is regarded as a superantigen, causing the immune system to release a large amount of cytokines that lead to significant inflammation.

Toxic shock syndrome toxin (TSST) is a superantigen with a size of 22 KDa produced by 5 to 25% of *Staphylococcus aureus* isolates. It causes toxic shock syndrome (TSS) by stimulating the release of large amounts of interleukin-1, interleukin-2, and tumor necrosis factor (TNF). In general, the toxin is not produced by bacteria growing in the blood; rather, it is produced at the local site of an infection, and then enters the blood stream.

TSST-1 is a prototype superantigen secreted by a *Staphylococcus aureus* bacterium strain in susceptible hosts, acts on the vascular system by causing inflammation, fever, and shock. The bacterium strain that produces TSST-1 lives mostly in the vagina of infected women (one-third of all TSS cases have been found in men).

Streptococcal mitogenic exotoxin Z (SMEZ) is one of the most potent superantigenic toxins produced by the streptococcal genome. The gene encoding SMEZ is present in all GAS strains studied. Although no clinical data are yet available demonstrating an association of SMEZ with GAS disease, the prevalence, potency, and antigenic variation shown by SMEZ suggest that this superantigen may have an important function in the pathogenesis of streptococcal disease.

As used herein, the term "lipopolysaccharide" (LPS), or "lipoglycan" refers to a large molecule consisting of a lipid and a polysaccharide joined by a covalent bond; LPS are found in the outer membrane of Gram-negative bacteria, act as endotoxins and elicit strong immune responses in animals. LPS is the major component of the Bacterial cell wall of Gram-negative bacteria, contributing greatly to the structural integrity thereof. LPS is an endotoxin, and induces a strong response from normal animal immune systems.

Therefore, in all aspects and embodiments of the disclosed subject matter said toxic bacterial components are selected from the group consisting of exotoxins, endotoxins, superantigen toxins, pathogen associated molecular patterns (PAMPs), Damage Associated Molecular Pattern molecules (DAMPs), lipopolysaccharides or toxic components thereof, molecules that are associated with groups of pathogens that are recognized by cells of the innate immune system and molecules that are associated with groups of pathogens that are recognized by Toll-like receptors (TLRs), but are not limited thereto.

Thus the pharmaceutical composition according to the presently disclosed subject matter can be used in the treatment of infections induced by Gram-negative bacteria selected from the group consisting of proteobacteria, *Escherichia coli*, *Salmonella*, *Shigella*, *Enterobacteriaceae*, *Pseudomonas*, *Moraxella*, *Helicobacter*, *Bdellovibrio*, *Stenotrophomonas*, acetic acid bacteria, *Legionella*, alpha-proteobacteria, *Wolbachia*, Gram-negative cocci, *Neisseria* species, *Neisseria gonorrhoeae*, *Neisseria meningitidis*, *Moraxella catarrhalis*, Gram-negative bacilli, *Hemophilus influenzae*, *Klebsiella pneumoniae*, *Legionella pneumophila*, *Pseudomonas aeruginosa*, *Proteus mirabilis*, *Enterobacter cloacae*, *Serratia marcescens*, *Helicobacter pylori*, *Salmonella enteritidis*, *Salmonella typhi*, *Acinetobacter baumannii*, *Francisella tularemia*, *Vibrio*, *vulnificus*, *cholerae*, *fluvialis*, *parahemolyticus*, *alginolyticus*, *Photobacter damsela*, *Aeromonas hydrophila*, *Clostridium perfringens*, *Clostridium histolyticum*, *Porphyromonas/prevotella* sp. *Prevotella Intermedia*, *Prevotella Buccae*, *Prevotella* sp., *Bacteroides uniformis* and NDM-1 bacterial strains, Gram-positive bacteria selected from the group consisting of Group A *streptococcus*, *S. pyogenes*, *S. pneumonia*, Group B strep, *Enterococcus faecalis*, Group D *streptococcus*, Group G *streptococcus*, *Streptococcus viridans*, *Streptococcus milleri*, *Propionibacterium* sp., *Enterococcus faecium*, *Peptostreptococcus* sp., *Streptococcus Microaerophilic*, *Lactobacillus* sp., *Staphylococcus Epidermis* and *Staphylococcus aureus*, or a combination thereof, toxic bacterial components selected from the group consisting of exotoxins, endotoxins, superantigenic toxins, pathogen associated molecular patterns (PAMPs), Damage Associated Molecular Pattern molecules (DAMPs), lipopolysaccharides, peptidoglycans or toxic components thereof, molecules that are associated with groups of pathogens that are recognized by cells of the innate immune system and molecules that are associated with groups of pathogens that are recognized by Toll-like receptors (TLRs).

Is specific embodiments, the at least one toxic bacterial component is a superantigenic toxin. In further specific embodiments the pharmaceutical composition as herein defined is wherein the at least one toxic bacterial component is a superantigenic toxin.

In the above and other embodiments of the disclosed subject matter, administration may be performed by any of the following routes: oral administration, intravenous, intramuscular, intraperitoneal, intranasal, intrathecal subcutaneous injection or said administration is by inhalation. Intravenous administration may be continuous administration, specifically over a period of from about 10 to about 30 minutes. Intravenous administration may alternatively be push administration.

In the above and other embodiments of the disclosed subject matter the pharmaceutical composition according to the invention is for any one of oral administration and parenteral administration.

In the above and other embodiments of the disclosed subject matter the pharmaceutical composition according to the invention is for any one of oral administration and intravenous, intramuscular, intraperitoneal, intranasal, intrathecal, subcutaneous injection or said administration is by inhalation.

In further embodiments of the presently disclosed subject matter the parenteral administration is any one of intravenous, intramuscular, intraperitoneal, intranasal, intrathecal, subcutaneous injection or said administration is by inhalation.

Further disclosed is a method of treating at least one of bacterial infection and acute inflammation associated therewith in a human subject in need, comprising administering to said subject a therapeutically effective amount of at least one peptide as defined herein or a composition comprising the same as defined herein. This method is also referred to herein as "method of treating".

The term "treat" or "treatment" or forms thereof as herein defined means to prevent worsening or arrest or alleviate or cure the disease or condition in a subject in need thereof.

The term "therapeutically effective amount" (or amounts) of the peptide for purposes herein defined is determined by such considerations as are known in the art in order to cure or at least arrest or at least alleviate the medical condition.

In some embodiments the therapeutically effective amount as herein defined is from about 0.1 to about 60 μg/Kg body weight of said subject.

Further disclosed is a method for eliciting in a human subject in need protective immunity against at least one of sepsis, toxic shock, septic shock, severe sepsis, incapacitation and resulting death, that are induced by a bacterial pathogen, a mixture of bacterial pathogens and/or at least one toxic bacterial component, said method comprising administering to said subject an immunologically effective amount of a peptide as defined herein or of a pharmaceutically acceptable composition comprising the same. In this method, the at least one toxic bacterial component may be selected from the group consisting of exotoxins, endotoxins, superantigenic toxins, pathogen associated molecular patterns (PAMPs), Damage Associated Molecular Pattern molecules (DAMPs), lipopolysaccharides, peptidoglycans or toxic components thereof, molecules that are associated with groups of pathogens that are recognized by cells of the innate immune system and molecules that are associated with groups of pathogens that are recognized by Toll-like receptors (TLRs), specifically superantigenic toxins. In specific embodiments the toxic bacterial component is, but not limited to, SEB, SMEZ or TSST-1. Efficacy of presently disclosed peptides against these toxins is shown in Example 1. This method is also referred to herein as "method of conferring immunity".

The term "immunologically effective amount" (or amounts) of the peptide mean any amount sufficient to confer immunity against sepsis, toxic shock, septic shock, severe sepsis, incapacitation and resulting death induced by pathogenic bacteria and/or toxic bacterial component/s and is determined by such considerations as are known in the art.

As shown in Example 3 below, the peptides according to the invention, e.g. peptides D-Ala-pB2-4, D-Ala-pB2-6 and D-Ala-pB2-7, were shown to block superantigen lethality in mice when the peptides were administered at a therapeutically effective amount ranging from 0.2 to 1 μg per mouse (see FIGS. 5A and 5B). This effective amount in a mouse weighing 25 gr corresponds to about 40 μg/kg, the human equivalent dose (HED) of which being 0.65 to 3.25 μg/kg.

Specific ranges used by the method of treating and method of conferring immunity disclosed herein can be from about 0.1 μg to about 60 μg peptide/kg body weight of said subject. Thus, in the above and other embodiments of the disclosed subject matter, the peptide according to the present disclosure is administered to said human subject in an amount of from about 0.1 to about 60 μg peptide/kg body weight of said subject.

Thus, the amount can be from 0.1 μg to 60 μg peptide/kg body weight of said subject, such as 0.1-60.0, 0.1-55.0, 0.1-40.0, 0.1-35.0, 0.1-30.0, 0.1-25.0, 0.1-20.0, 0.1-15.0, 0.1-10.0, 0.1-9.0, 0.1-8.0, 0.1-7.0, 0.1-6.0, 0.1-5.0, 0.1-4.0, 0.1-3.0, 0.1-2.0, 0.1-1.0, 0.1-0.75, 0.1-0.5, 0.1-0.25. Specifically, the therapeutically effective amount may be any one of 0.25, 0.5, 0.65, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 12.5, 15.0, 17.5, 20.0, 25.0, 30.0, 35.0, 40.0, 45.0, 50.0, 55.0 or 60.0 μg peptide/kg body weight of said subject.

It is to be noted that the amount of the peptide to be administered may vary by about 5-25%, in consideration of the molecular weight and other features of a specific peptide. Thus the term "about" as herein defined refers to a fluctuation of 5-25% of the amount as herein defined.

In the above and other embodiments of the disclosed subject matter, the peptide for use in treatment of bacterial infection and/or acute inflammation associated therewith according to the present disclosure may be administered at a suitable time post onset of said at least one of infection and acute inflammation associated therewith. Alternatively or additionally, the peptide for use according to the present disclosure may be administered immediately following the onset of said infection or acute inflammation associated therewith. The peptide according to the present disclosure may be administered during the acute phase of the infection, and if necessary, also thereafter, as may be determined by the attending physician.

The term "onset" refers to any time point between the time of infection of said human subject or the time of beginning of its clinical manifestation or the manifestation of acute inflammation associated with or resulting from said infection and the time of diagnosis of any of the infection and inflammation by a skilled member of attending medical staff, and any time there-between or thereafter, in which treatment in accordance with the present disclosure is professionally assigned to said subject.

As used herein, the term "human subject in need" is to be taken to mean a human suffering from at least one of infection and acute inflammation associated therewith as herein defined. The "human subject in need" may be a human subject suffering from sepsis, toxic shock, septic shock, severe sepsis and/or incapacitation that may result in death, that are induced by lethal bacterial pathogen/s and/or toxic bacterial component/s of bacterial pathogen/s. The "human subject in need" may also be a human at risk of being inflicted by bacterial infection and acute inflammation associated therewith.

In the above and other embodiments of the disclosed subject matter, the pharmaceutical composition or method of treating according to the invention optionally further comprises administering to said human subject in need an additional therapeutic agent.

In the above and other embodiments of the disclosed subject matter the additional therapeutic agent can be any one of antibacterial agent, antiviral agent, antifungal agent, antibiotic agent, bacteriostatic and bactericidal agent, steroid and antimicrobial agent.

In the above and other embodiments of the disclosed subject matter, said peptide and said additional other therapeutically effective agent are administered simultaneously. Alternatively or additionally, said peptide and said additional other therapeutically effective agent are administered at different time points, at different intervals between administrations, for different durations of time, or in a different order.

For example, treatment may commence with administration of both the peptide and the additional other agent, and administration of the additional agent may be ceased before or after the administration of the peptide.

In the above method of conferring to a subject protective immunity against at least one of sepsis, toxic shock, septic shock, severe sepsis, incapacitation and resulting death, that are induced by a bacterial pathogen, a mixture of bacterial pathogens and/or at least one toxic bacterial component, the peptide according to the present disclosure may specifically be administered at a suitable time before challenge with said bacterial pathogen/s and/or toxic bacterial component/s, or thereafter. When administered before challenge, the peptide may be administered at about 30, 25, 20, 15 minutes or less before challenge. When administered after challenge, the peptide is administered immediately or shortly thereafter.

It is appreciated that certain features of the presently disclosed subject matter, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Peptides

Peptides were synthesized using fluoronyl-methoxycarbonyl chemistry, cleaved and the side chain deprotected with triflouroacetic acid. Peptides were >95% pure by high-pressure liquid chromatography; molecular weight was verified by MALDI-TOF mass spectrometry. Peptides were abutted with D-Ala (D-Alanine) at both termini for greater protease resistance in biological assays and with Cys (Cysteine) for Surface Plasmon Resonance (SPR). B7-2 peptides were dissolved readily into RPMI 1640 tissue culture medium.

Antibodies

αSEB monoclonal antibody (Toxin Technology: clone MB2B33), horseradish peroxidase-conjugated goat anti-mouse IgG or donkey anti-goat (KPL), mouse monoclonal αCD28 (clone 37407), αCD3 (clone UCHT1), goat polyclonal anti-CD28 and anti-B7-2 (R&D Systems) antibodies were used. Binding of SEB to immobilized B7-2-Fc and ribonuclease A was assayed in enzyme-linked immunosorbent assays using corresponding horseradish peroxidase-conjugated mouse anti-SEB monoclonal antibody.

Induction of Cytokine Gene Expression

Human peripheral blood mononuclear cells (PBMC) from healthy human donors were separated on Ficoll Paque (Amersham), washed twice with 50 ml of RPMI 1640 medium, resuspended at $4 \times 10^6$ cells/ml and cultured in this medium supplemented with 2% fetal calf serum, 2 mM glutamine, 10 mM MEM nonspecific amino acids, 100 mM Na-pyruvate, 10 mM Hepes pH 7.2, $5 \times 10^{-5}$ M 2-mercaptoethanol, 100 U/ml penicillin, 100 µg/ml streptomycin and 5 µg/ml nystatin. Staphylococcal enterotoxin B (SEB, Lot 1430, Department of Toxinology, U.S. Army Medical Research Institute of Infectious Diseases) (10, 12) was added to a final concentration of 100 ng/ml. Mouse antihuman monoclonal antibodies αCD3 (clone UCHT1; 100 ng/ml) and αCD28 (clone 37407; 2.5 g/ml) (R&D Systems, Minneapolis, Minn.) were used as inducers. The E. coli Lipopolysaccharide (LPS) 0111:B4 for studies with human PBMC was obtained from Sigma Aldrich (St. Louis, Mo.). Secreted cytokines were quantitated in triplicate with Quantikine ELISA kits (R&D Systems) and are presented as means±SEM.

B7-2 Expression Vectors

A vector expressing B7-2 was generated by cDNA synthesis of human CD86 (NM_175862) from total human PBMC RNA using Verso RT-PCR kit (ABgene). CD86 cDNA was generated using KOD polymerase (Novagen) with the phosphorylated PCR primers 5'-GACGTCGACGGAAGGCTTGCACAGGGT (denoted by SEQ ID NO:51) and 5'-CACGCGGCCGCCCAGGTCATGAGCCATTAAGC (denoted by SEQ ID NO:52). The PCR product was inserted into pEGFP-N3 DNA (Clontech) that had been digested with SalII and NotI and lacked the GFP region, using Fast-Link DNA Ligation Kit (Epicentre).

Vectors expressing B7-2 fused C-terminally to GFP or Cherry were generated from B7-2 cDNA vector template with the phosphorylated PCR primers 5'-TACTCGAGATGGGACTGAGTAACATTC (denoted by SEQ ID NO:53) and 5'-GTCCGCGGTGAAGCATGTACACTTTTGTCG (denoted by SEQ ID NO:54), deleting the B7-2 termination codon. Upon digestion with XhoI and SacII, the PCR product was inserted either into pEGFP-N3 DNA or pmCherry-N1 DNA (Clontech). B7-2C/Cherry vector was generated from B7-2/Cherry template using the primers 5'-GTCTCTCGTCCTTCCGG (denoted by SEQ ID NO:55) and 5'-CTAACTTCAGTCAACCTG (denoted by SEQ ID NO:56).

TABLE 1

Sequences of primers

| SEQ ID NO: | Sequence | Description |
|---|---|---|
| SEQ ID NO: 51 | GACGTCGACGGAAGGCTTGCACAGGGT | Primer for B7-2 cloning |
| SEQ ID NO: 52 | CACGCGGCCGCCCAGGTCATGAGCCATTAAGC | Primer for B7-2 cloning |
| SEQ ID NO: 53 | TACTCGAGATGGGACTGAGTAACATTC | Primer for preparing B7-2-GFP fusion construct |
| SEQ ID NO: 54 | GTCCGCGGTGAAGCATGTACACTTTTGTCG | Primer for preparing B7-2-GFP fusion construct |

TABLE 1-continued

Sequences of primers

| SEQ ID NO: | Sequence | Description |
|---|---|---|
| SEQ ID NO: 55 | GTCTCTCGTCCTTCCGG | Primer for preparing B7-2C/Cherry vector |
| SEQ ID NO: 56 | CTAACTTCAGTCAACCTG | Primer for preparing B7-2C/Cherry vector |

CD28B7-2 Interaction

In order to assay the effect of SEB on binding of B7-2 to CD28 on the cell, HEK293T cells were transfected to express cell-surface CD28 (10) or with empty vector expressing GFP. After 36 hours, the cells were incubated for 45 minutes with 0.2 µg/ml soluble B7-2 in the absence or presence of SEB. After three washes with cold phosphate-buffered saline, cells were lysed. Equal amounts of total cell protein (Bradford assay) were subjected to 10% polyacrylamide gel electrophoresis (PAGE) and western blotting to show binding of B7-2 and expression of CD28 by the cells. Conversely, the effect of SEB on binding of CD28 to B7-2 on the cell was assayed by transfecting HEK293T cells to express cell-surface B7-2. After 36 hours, the cells were incubated for 45 minutes with 0.2 μg/ml soluble CD28 in the absence or presence of SEB. After three washes as above, cells were lysed. Equal amounts of total cell protein were subjected to 10% PAGE and Western blotting to show binding of CD28 and expression of B7-2 by the cells.

Recombinant Superantigens

Chromosomal DNA isolated from *S. aureus* COL, from a TSST-1-producing strain of *S. aureus*, and from a SMEZ-producing strain of *Streptococcus pyogenes* was used to clone wt SEB, TSST-1 and SMEZ genes, respectively, into pHTT7K (14). Each one of the above genes was expressed in *E. coli* as the mature proteins with an N-terminal $His_6$-tag. Inserts were verified by DNA sequencing. Total protein was loaded onto a His-Bind column (Novagen) and eluted stepwise with imidazole. Recombinant proteins recovered after dialysis were >98% pure on SDS-PAGE and >98% homogeneous as monomer upon analytical gel filtration through a 1×30 cm Superdex 75 column calibrated with molecular weight standards (GE Healthcare-Amersham Pharmacia) from which protein was eluted at a flow rate of 1 ml/min. Recombinant SEB was lethal to mice at 10 μg/ml.

Surface Plasmon Resonance Spectroscopy

Proteins and peptides were diluted to 10-200 μg/ml in 10 mM Na acetate pH 4.0 and immobilized on a CM5 sensorchip using amine coupling kit and amine-thiol coupling kit (BIAcore), respectively. Analytes were injected at 20 l/min in 25 mM HEPES pH 7.4, 150 mM NaCl, 3.4 mM EDTA, and 0.005% surfactant P20 under low ligand density conditions that minimize mass transfer limitations; a maximal binding capacity of the immobilized ligand in the range of 50-150 response units enables measurement of binding kinetics. Regeneration was with 50 mM phosphoric acid. Kinetic analyses were performed at 25° C. in a BIAcore 3000 instrument, deducting the control flow cell signal from the binding signal. Analyte curves were run in duplicate; representative results are shown. BIAevaluation 3.1 software was used to determine $K_D$ in the linear ligand concentration range (1:1 Langmuir binding). Criteria for $K_D$ determination for complexes were standard error as percent of $k_a$ and $k_d$; $\lambda^2$ values well below 2 show the quality of fit between calculated and observed binding values and attest to the purity of the ligands examined. Fitting residuals were within the range of ±2, validating the goodness of fit. Human IgG (Jackson Laboratories) and ribonuclease A (Sigma) served as controls.

Mouse Lethality Assay

Female BALB/c mice (10-12 weeks; Harlan) were challenged by intraperitoneal injection of SEB and 20 mg D-galactosamine to sensitize the animals to superantigens (12). Antagonist peptides were injected intraperitoneally 30 min before challenge. Survival was monitored. Viability remained constant beyond 72 hours for as long as monitored (two weeks). Experiments involving mice were approved by the institutional animal care and use committee.

Statistical Analysis

Survival curves were analyzed using the Kaplan-Meier method, with the Log-Rank test for comparisons.

Structure Models

Cartoon models of protein structure were created in PyMol (<www.pymol.org>).

Example 1

B7-2 Uses its Homodimer Interface to Bind SEB

In the B7-2/CTLA-4 complex (1), the MYPPPY domain as denoted by SEQ ID NO: 59, conserved between CD28 and CTLA-4, engages B7-2 such that the B7-2 dimer interface remains fully accessible. Accordingly, short peptides termed herein D-Ala-pB2-4 (having the amino acid sequence (D-A)EKFDSVHSKYM(D-A) denoted by SEQ ID NO: 6) and D-Ala-pB2-6 (having the amino acid sequence (D-A)DSDSWTLR(D-A) denoted by SEQ ID NO: 10) overlapping residues in the B7-2 crystallographic homodimer interface were synthesized. The peptides are shown in FIG. 1 on the B7-2 dimer interface region. FIG. 1 shows a variant of SEQ ID NO:13, having the amino acid sequence denoted by SEQ ID NO:50, in which the N-terminal Pro was replaced by Met. As controls, peptides termed herein D-Ala-pB2-2 (having the amino acid sequence (D-A) DLPCQFANSQN(D-A) denoted by SEQ ID NO: 2), D-Ala-pB2-3 (having the amino acid sequence (D-A)HHKKPTGMIR(D-A) denoted by SEQ ID NO: 4) and D-Ala-pB2-5 (having the amino acid sequence (D-A)MLKIQAY(D-A) denoted by SEQ ID NO: 8) were synthesized, where these peptides fall outside the dimer interface (as shown in FIG. 1).

As shown in FIG. 2A, D-Ala-pB2-2, D-Ala-pB2-3 and D-Ala-pB2-5 failed to inhibit SEB-mediated induction of IFN-γ in PBMC whereas D-Ala-pB2-4 and D-Ala-pB2-6 were strongly inhibitory. D-Ala-pB2-4 and D-Ala-pB2-6, but not the other three peptides, inhibited also induction of IL-2 and TNF-α (FIG. 2B). While at lower concentrations (0.01 μg/ml), pB2-4 and pB2-6 inhibited IL-2, IFN-γ and TNF-α induction only partially, together they showed pronounced synergistic inhibition (FIG. 2C). By contrast, IL-10 induction was resistant to D-Ala-pB2-4 and D-Ala-pB2-6, alone or in combination.

Synergy between D-Ala-pB2-4 and D-Ala-pB2-6 might be derived from the fact that they cover non-overlapping parts of the B7-2 dimer interface (as schematically shown in FIG. 1). Therefore their activity was next compared to that of a peptide termed herein D-Ala-pB2-7 having the amino acid sequence (D-A)MGRTSFDSDS(D-A) denoted by SEQ ID NO: 12, which partially overlaps D-Ala-pB2-4 and D-Ala-pB2-6, covering a continuous homodimer interface domain of nine amino acids (FIG. 1). As shown in FIG. 2D, pB2-7 inhibited SEB-mediated induction of IL-2, IFN-γ and TNF-α to a comparable extent as that of D-Ala-pB2-4 and D-Ala-pB2-6 in combination and like them, did not inhibit induction of IL-10.

Interestingly, as demonstrated in FIG. 2E, similar results were also obtained with streptococcal mitogenic exotoxin Z (SMEZ, FIG. 2E1, FIG. 2E2, FIG. 2E3 and FIG. 2E4) which is known to be 40-fold more lethal than SEB and with toxic shock syndrome toxin-1 (TSST-1, FIG. 2E5, FIG. 2E6 and FIG. 2E7), a superantigen having only 6% sequence identity with SEB but structurally conserved in the β-strand(8)/hinge/α-helix(4) domain (12).

The ability of B7-2 dimer interface mimetic peptides to inhibit signaling for inflammatory cytokine induction by divergent superantigens suggested that these peptides compete with B7-2 in binding superantigen. Indeed, as shown in FIG. 3A and FIG. 3B, the peptides D-Ala-pB2-4 and D-Ala-pB2-6, respectively, each bound SEB directly, with a $K_D$ in the micromolar range (Table 2, below). D-Ala-pB2-4 and D-Ala-pB2-6 similarly bound TSST-1 and SMEZ (FIG. 3C and FIG. 3D for binding TSST-1 and FIG. 3E and FIG. 3F for binding SMEZ) with micromolar affinity (Table 2 below). Thus, superantigens engage the homodimer interface located within the V domain of B7-2.

In Table 2 below, purified recombinant superantigens were used and concentrations of SEB ranged from 0.78 μM in six twofold increments, concentrations of TSST-1 ranged from 0.0625 μM in five twofold increments and concentrations of SMEZ ranged from 0.0625 μM in four twofold increments.

showing specificity. Interestingly, alone or in combination, the B7-2 dimer interface mimetic peptides D-Ala-pB2-4 and D-Ala-pB2-6 effectively blocked binding of SEB to cells expressing B7-2, whereas the peptide D-Ala-pB2-2, which falls outside the dimer interface, did not inhibit binding (FIG. 4A). The peptide D-Ala-pB2-7 likewise blocked binding of SEB to cells expressing B7-2, whether alone or in combination with D-Ala-pB2-4 (FIG. 4B).

The finding that B7-2 dimer interface mimetic peptides specifically block binding of SEB to cell-surface B7-2 shows that the SEB binding site in cell-surface B7-2 is the dimer interface and strongly reinforces the results showing that these peptides bind superantigens directly and inhibit inflammatory cytokine induction.

Remarkably, D-Ala derivatives of the p2TA and p1TA peptides (having the core amino acid sequence SPMLVAYD denoted herein by SEQ ID NO: 16 and HVKGKHLCP denoted herein by SEQ ID NO: 17, respectively) derived from the CD28 homodimer interface that bind the superantigen directly, inhibiting inflammatory cytokine induction and toxicity (10), equally inhibited binding of SEB to cells expressing B7-2 (FIG. 4B and FIG. 4C). Because p2TA and p1TA bind SEB in its β-strand(8)/hinge/α-helix(4) domain (10), they compete with B7-2 for its binding site in the superantigen.

In a reciprocal experiment, cells were transfected to express cell-surface CD28. It was previously reported that binding of SEB to such cells is abrogated by αCD28, p1TA and p2TA but not by cB7-2 (10). Indeed, the peptides

TABLE 2

| | | Kinetic parameters of Surface Plasmon Resonance analysis | | | | | | |
|---|---|---|---|---|---|---|---|---|
| Ligand | Analyte | $K_a$ (1/Ms) | s.e.m. ($K_a$) | % s.e.m. ($K_a$)/$k_a$ | $K_d$ (1/s) | s.e.m. ($k_d$) | % s.e.m. ($K_d$)/$k_d$ | KD (μM) | $X^2$ |
| pB2-4 | SEB | 413 | 10.30 | 2.50 | 9.58E−04 | 4.59E−05 | 4.80 | 2.32 | 1.05 |
| pB2-6 | SEB | 491 | 8.79 | 1.80 | 1.9E−03 | 3.69E−05 | 1.94 | 3.90 | 1.07 |
| pB2-4 | TSST-1 | 4,080 | 159.00 | 3.90 | 2.77E−02 | 8.00E−05 | 2.89 | 9.80 | 0.24 |
| pB2-6 | TSST-1 | 2,530 | 95.40 | 3.77 | 3.04E−03 | 5.92E−05 | 1.95 | 1.20 | 0.20 |
| pB2-4 | SMEZ | 3,020 | 85.00 | 2.81 | 2.93E−03 | 9.32E−05 | 3.18 | 7.30 | 0.40 |
| pB2-6 | SMEZ | 1,590 | 50.60 | 3.18 | 2.86E−03 | 1.34E−04 | 4.69 | 1.79 | 0.12 |

$K_a$, association rate; $k_d$, dissociation rate.

In order to obtain the parameters shown in Table 2 above, purified recombinant superantigens were used. Concentrations of SEB ranged from 0.78 μM in six twofold increments; concentrations of TSST-1 ranged from 0.0625 μM in five twofold increments; and concentrations of SMEZ ranged from 0.0625 μM in four twofold increments. $k_a$, association rate; $k_d$, dissociation rate. BIAevaluation 3.1 software (BIAcore) was used to determine KD in the linear ligand concentration range (1:1 Langmuir binding). Criteria for KD determination for complexes were standard error as percent of $k_a$ and $k_d$; $\lambda^2$ values well below 2 show the quality of fit between calculated and observed binding values and attest to the purity of the ligands examined. Fitting residuals were within the range of ±2, validating the goodness of fit.

Example 2

Binding of SEB to B7-2 or CD28: Reciprocal Inhibition by Dimer Interface Peptides Next, binding of SEB to a cell population expressing B7-2 was studied. As shown in FIG. 4A, binding of SEB was abrogated by cB7-2 antibody but not by cCD28, a monoclonal antibody that targets a CD28 dimer interface epitope, D-Ala-pB2-4, D-Ala-pB2-6 and D-Ala-pB2-7, but not the control peptide D-Ala-pB2-2, were as capable of blocking binding of SEB to cell-surface CD28 as CD28 dimer interface mimetics p1TA and p2TA (FIG. 4D).

Thus, the superantigen not only uses its conserved β-strand(8)/hinge/α-helix(4) domain to bind to either B7-2 or CD28 at their dimer interface but peptide mimetics of either dimer interface possess dual antagonist activity, blocking binding of superantigen to either receptor in a reciprocal manner.

Example 3

B7-2 Dimer Interface Peptides Protect from SEB Lethality

Next, an accepted model for superantigen lethality, D-galactosamine-sensitized mice was used for demonstrating the effect of the peptides D-Ala-pB2-4, D-Ala-pB2-6 and D-Ala-pB2-7 on SEB-challenged mice (10 and 12). As shown in FIG. 5A, D-Ala-pB2-4 and D-Ala-pB2-6 blocked superantigen lethality. Whereas only ⅕ of the control mice survived SEB challenge, ⅘ and 5/5 of the mice that received D-Ala-pB2-4 and D-Ala-pB2-6, respectively, at time of exposure to SEB survived (FIG. 5A). Notably, the peptide D-Ala-pB2-7 protected when present in only 2- to 3-fold molar excess over SEB (FIG. 5B). This high efficacy supports a critical role for the B7-2 dimer interface in mediating the deleterious response to superantigens.

Example 4

Attenuation of CD28 Signaling by Peptides Derived from the B7-2 Dimer Interface

The effect of the peptide D-Ala-pB2-7 was also examined in human PBMC induced by αCD3, as described above. As shown in FIG. 6A and FIG. 6B, D-Ala-pB2-7 did not inhibit the induction of IFN-γ by αCD3, whether the peptide was present at 1 μg/ml (FIG. 6A) or a tenfold higher concentration of 10 μg/ml (FIG. 6B), showing that it does not block signaling through the T cell receptor. Moreover, at neither concentration, namely 1 or 10 μg/ml did D-Ala-pB2-7 induce a response by itself (FIG. 6A and FIG. 6B, respectively).

However, as shown in FIG. 7A and FIG. 7B, pB2-7 attenuated the expression of IFN-γ (FIG. 7A) and TNF-α (FIG. 7B) when the expression of these cytokines was induced by αCD3 jointly with αCD28. Interestingly, a significant attenuation of the expression of each of IFN-γ and TNF-α was observed at low peptide concentrations of 0.01 and even 0.001 μg/ml, attesting to potent inhibition. Thus, the peptide inhibits signaling for an inflammatory cytokine response when it is transduced through CD28. As shown in FIG. 8, inhibition of CD28 signaling was also shown for the cytokines IFN-γ and TNF-α by the peptide D-Ala-pB2-4, which like D-Ala-pB2-7 is derived from the homodimer interface of B7-2, but not by D-Ala-pB2-2, which falls outside the dimer interface domain.

Example 5

Attenuation of LPS Signaling by the Peptides pB2-4, pB2-6 and pB2-7

Lipopolysaccharide (LPS) is a virulence factor specific for Gram-negative bacteria and more generally is a hallmark of Gram-negative infection. As shown in FIG. 9A, induction of TNF-α expression in human PBMC by *E. coli* LPS was sensitive to attenuation by the B7-2 dimer interface mimetic peptides D-Ala-pB2-4, D-Ala-pB2-6 as well as by their combination. The effect of the B7-2 dimer interface mimetic peptide pB2-7 is shown in FIG. 9B.

The greater extent of inhibition demonstrated in FIG. 9A for the combination of D-Ala-pB2-4 with D-Ala-pB2-6 (versus the effect of each one of the peptides alone) reflects its greater superantigen antagonist activity, consistent with the results shown above.

Remarkably, as shown in FIG. 10, induction of TNF-α expression in human PBMC induced by *E. coli* LPS was reduced by each one of the peptides D-Ala-pB2-4, D-Ala-pB2-6 and D-Ala-pB2-7 even when the peptides were present at a concentration of 0.01 μg/ml. Thus, a low concentration of B7-2 dimer interface mimetic peptide suffices to attenuate LPS-mediated TNF-α induction.

Example 6

The Potency of B7-2 Dimer Interface Mimetic Peptides

The B7-2 dimer interface has no known role in co-stimulation and is structurally well separated from the CD28 binding site. Within a receptor homodimer interface, weak, short-range Van der Waals interactions coupled with steric fit enable receptor homodimerization and prevent the generation of heterodimers. Engagement of a superantigen should displace contacts between the B7-2 monomers, which unlike CD28 are not linked through an intermolecular disulfide bond outside the dimer interface and thus require a second-order binding reaction to redimerize. This may explain the ability of D-Ala-pB2-7 to protect mice from lethal SEB challenge even at low molar ratio to the toxin as shown above.

B7-2 dimer interface mimetic peptides may bind back into the self-adhesive B7-2 receptor homodimer interface from which they are derived, and thereby attenuate signaling even in the absence of a superantigen, as shown in FIG. 7, FIG. 8 and FIG. 9. Peptide efficacy is enhanced by the lack of an intermolecular disulfide bond between the B7-2 monomers, facilitating their separation by a competing short peptide. This may account for the efficacy of B7-2 dimer interface mimetic peptides against excessive immune stimulation observed in the absence of a superantigen.

Example 7

Peptides Derived from the B7-1 Homodimer Interface

B7-1 is homologous to B7-2, where both B7-1 and B7-2 act as co-stimulatory ligands expressed on the surface of antigen presenting cells (APCs). FIG. 11 shows the peptides derived from the B7-1 homodimer interface (MNIWPEYKNRTIFDITNNLSIV, as denoted by SEQ ID NO: 57), namely pB1-4, pB1-6, pB1-7 and pB1-8 denoted by SEQ ID NO: 38, SEQ ID NO: 42, SEQ ID NO: 40 and SEQ ID NO: 48, respectively. FIG. 12 schematically shows alignment of segments derived from the dimer interface of both human B7-1 (SEQ ID NO: 57) and human B7-2 (EKFDSVHSKYMGRTSFDSDSWTLR, as denoted by SEQ ID NO: 58), with conserved residues indicated by bold letters and residues participating in the B7-2 dimer interface indicated by underlining. FIG. 12 also shows the human B7-2 peptides pB2-4, pB2-7 and pB2-6 aligned with the peptides pB1-4, pB1-7 and pB1-6 in part of the B7-1 sequence. The effect of the peptides derived from human B7-1 dimer interface on cytokine levels as a result of various inductions, for example, superantigen challenge, will be also examined.

Example 8

Model of Polymicrobial Infection: Cecal Ligation and Puncture (CLP)

The murine cecal ligation and puncture (CLP) model is a clinically relevant model to investigate polymicrobial infections and follow the effects of therapeutic agents on intra-abdominal infections or sepsis. Specific pathogen-free BALB/c mice (8-12 weeks) and CD1 outbred mice (8-12 weeks) are obtained. All animal studies are approved by Institutional Animal Care and Use Committees (IACUC) before experiments are initiated.

The animals are anesthetized with inhaled isoflurane (Baxter Pharmaceutical Products Inc., Deerfield, Ill.) (induction at concentration of 4-5%+0.8-1 L/min, maintenance at 1-3%+0.8-1 L/min).

The cecum is exteriorized through a 1.5 cm midline incision and ligated with a 5-0 nylon monofilament suture, at 90% of its length just distal to the ileocecal junction. The cecum is then punctured twice using a 23 gauge needle along the ante-mesenteric side of the cecum. Patency is assured by expressing a scant amount of laminal contents through puncture site. The organ is returned to the abdominal cavity, fascia and skin are closed, and topical lidocaine and bacitracin are applied at the surgical site. Each animal receives 20 mg/kg intramuscular dose of moxifloxacin (representing suboptimal dose of $LD_{25}$) and 1 ml subcutaneous bolus of normal saline. The animals are allowed to be re-warmed until fully conscious and are then returned to their cages.

Tested peptides are specifically D-Ala-pB2-7 (as denoted by SEQ ID NO: 12), D-Ala-pB2-2 (as denoted by SEQ ID NO:2), D-Ala-pB2-6 (as denoted by SEQ ID NO:10), D-Ala-pB1-4 (as denoted by SEQ ID NO:39), D-Ala-pB1-7 (as denoted by SEQ ID NO:41), D-Ala-pB1-6 (as denoted by SEQ ID NO:43), D-Ala-pB1-8 (as denoted by SEQ ID NO:49), administered intravenously.

The efficacy of these peptides according to the invention, when given intravenously (i.v.) is tested and animals are followed daily for a total of 7 days for overt signs of sepsis and survival. Any moribund animals (defined as hypothermic <30° C. and unable to maintain normal body posture) are euthanized and scored as lethally-infected animals. At the end of day 7, survivors are euthanized, and are examined for quantitative microbiology of organ tissues (blood, peritoneum, liver, lung, and spleen).

Dose response relationships of a peptide of the invention, when administered to animals subjected to CLP is examined. Animals are treated with different doses of the peptide of the invention, about 2 hours after the surgery. Suboptimal dose of moxifloxacin ($LD_{25}$) may be given at time 0, to some or all of the animals. Animals are followed up for several days and survival rates are determined.

The potential effect of the peptides on cytokine and chemokine production following CLP is further investigated.

Balb/c mice are subjected to CLP and are treated with a peptide according to the invention at about 2 hours post surgery, without any addition of antibiotics. Mice (treated and control non-treated, as well as sham-operated animals, which serve as additional control) are euthanized at 12 and 24 hours post surgery, and blood is collected in heparinized syringes by cardiac puncture. Plasma is then obtained by centrifugation and stored at −70° C. until analyzed. Peritoneal fluids are obtained from mice by lavage, clarified by centrifugation and stored at −70° C. until analyzed. As a representative of Th1 cytokines, the levels of TNF-α are measured, and as representatives of chemokines that are associated with pro-inflammatory response, the levels of RANTES and KC are measured in both blood (plasma) and the local infection site (peritoneal fluid) of the peptide-treated animals.

The levels of additional cytokine/chemokine in the peritoneum and blood following CLP are evaluated. These include TNF-α, IL-6, IL-17A, IL-10, Rantes, MCP-1 and KC in the peritoneal fluid and plasma taken about 12 or about 24 hours after CLP.

Animals subjected to CLP exhibit high load of bacteria in the blood and peritoneal fluid. Bacteria usually invade the blood from the peritoneal fluid, and are primarily killed by circulating polymorph nuclear cells (PMN) that recognize bacterial elements bound to macrophage surfaces and secondarily by the resident macrophages themselves. From the blood bacteria migrate to the liver and spleen (which are the primary sites for clearance of bacteria from the systemic circulation), where they are picked up by resident macrophages. To study the potential effect of the peptides of the invention on the bacterial load, the dissemination of bacteria in these tissues/organs is measured. Mice are subjected to CLP and are divided into groups (n=6-8 in each group), that are either treated by the peptide about 2 hours post CLP, or injected with PBS and serve as control, or are sham-operated. None of the animals receives antibiotics. Mice are euthanized after about 12 and about 24 hours from surgery, and tissue samples are obtained from the blood, peritoneal fluid, liver kidney and spleen of each animal. Levels of bacteria are measured by colony counts and compared between the treated and control groups.

Keratinocyte chemokine (KC) is an important component responsible for recruitment and accumulation of polymorph nuclear cells (PMN) into target organs that have been implicated as key process in the development of systemic inflammation during sepsis, leading to organ dysfunction. Therefore, the levels of PMN are evaluated in the spleen, liver and kidney of animals post CLP, and are measured by the activity of myeloperoxidase (MPO), which is a key enzyme associated with PMN activity, serving as an indirect marker for the presence of neutrophils. MPO activity is measured in homogenized tissues at about 12 and about 24 hours post CLP. Readout is performed spectrophotometrically at 460 nm, for 10 min, in one minute intervals.

Further support for the reduced levels of PMN in key organs is exemplified by direct counting of PMN in histological slides, obtained from specific tissues of animals post CLP, after immunohistochemical staining, for assessment of neutrophil influx. Formalin-fixed paraffin sections obtained from CLP animals at 24 hours post CLP, are stained with Naphthol AS-D chloroacetate esterase (leukocyte-specific esterase), counter-stained with Gills hematoxylin solution and coverslipped. Numbers of neutrophils (esterase positively stained cells) present in the liver sections are randomly screened (5-7 fields/sample) microscopically, at ×400.

To determine if treatment with the peptides of the invention affects the expression of CD28 on immune effector cells, the peripheral blood cells and splenocytes are examined about 12 and about 24 hours following surgery.

To test the effect of the peptides of the invention on cell proliferation, ex vivo experiments are performed with isolated splenocytes taken from sham, CLP mice treated with or without the peptide, stimulated with anti-CD3 alone or anti-CD3+anti-CD28 antibodies and cultured for 72 hours. The splenocyte proliferation index is determined and compared to cells taken from sham animals.

Increased apoptotic processes in key organs such as kidney, liver and spleen, play a determining pathogenic role in the outcome of sepsis, contributing to organ failure. Therefore, the potential effect of treatment with the peptides of the invention on renal and spleen apoptosis in animals subjected to CLP is studied. Apoptosis is determined in histological slides taken from animals at about 24 hours post CLP using TUNEL staining. Slides are examined under a fluorescent microscope for evidence of apoptosis.

To compare the extent of sepsis-induced apoptosis following CLP between peptide-treated and vehicle-treated mice, isolated splenocytes are also stained with an early apoptotic marker, Annexin V, combined with cell surface marker (CD3, CD4, CD8, B220, Gr-1) and analyzed by flow cytometry.

TABLE 3

Sequences referred to herein

| SEQ ID NO. | Sequence | Description |
|---|---|---|
| SEQ ID NO. 1 | DLPCQFANSQN | pB2-2 |
| SEQ ID NO. 2 | (D-A)DLPCQFANSQN(D-A) | D-Ala-pB2-2 |
| SEQ ID NO. 3 | HHKKPTGMIR | pB2-3 |
| SEQ ID NO. 4 | (D-A)HHKKPTGMIR(D-A) | D-Ala-pB2-3 |
| SEQ ID NO. 5 | EKFDSVHSKYM | pB2-4 |
| SEQ ID NO. 6 | (D-A)EKFDSVHSKYM(D-A) | D-Ala-pB2-4 |
| SEQ ID NO. 7 | MLKIQAY | pB2-5 |
| SEQ ID NO. 8 | (D-A)MLKIQAY(D-A) | D-Ala-pB2-5 |
| SEQ ID NO. 9 | DSDSWTLR | pB2-6 |
| SEQ ID NO. 10 | (D-A)DSDSWTLR(D-A) | D-Ala-pB2-6 |
| SEQ ID NO. 11 | MGRTSFDSDS | pB2-7 |
| SEQ ID NO. 12 | (D-A)MGRTSFDSDS(D-A) | D-Ala-pB2-7 |
| SEQ ID NO. 13 | PLKIQAYFNE TADLPCQFAN SQNQSLSELV VFWQDQENLV LNEVYLGKEK FDSVHSKYMG RTSFDSDSWT LRLHNLQIKD KGLYQCIIHH KKPTGMIRIH QMNSELSVLA | Fragment of human B7-2 |
| SEQ ID NO. 14 | FCSGVIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA | B7-1, CD80 antigen (CD28 antigen ligand 1, B7-1 antigen), isoform CRA_a (Accession No. EAW79564) |
| SEQ ID NO. 15 | YNKKKATVQELD | p12A |
| SEQ ID NO. 16 | SPMLVAYD | p2TA |
| SEQ ID NO. 17 | HVKGKHLCP | p1TA |
| SEQ ID NO. 18 | FNETADLP | A peptide derived from B7-2 homodimer interface |
| SEQ ID NO. 19 | (D-Ala)FNETADLP(D-Ala) | A peptide derived from B7-2 homodimer interface, abutted by D-Ala on both termini |
| SEQ ID NO. 20 | NQSLSELV | Peptide derived from B7-2 homodimer interface |

TABLE 3-continued

Sequences referred to herein

| SEQ ID NO. | Sequence | Description |
|---|---|---|
| SEQ ID NO. 21 | (D-Ala)NQSLSELV(D-Ala) | A Peptide derived from B7-2 homodimer interface, abutted by D-Ala on both termini |
| SEQ ID NO. 22 | YLGKEKFD | Peptide derived from B7-2 homodimer interface |
| SEQ ID NO. 23 | (D-Ala)YLGKEKFD(D-Ala) | A Peptide derived from B7-2 homodimer interface, abutted by D-Ala on both termini |
| SEQ ID NO. 24 | TLRLHNLQ | Peptide derived from B7-2 homodimer interface |
| SEQ ID NO. 25 | (D-Ala)TLRLHNLQ(D-Ala) | A Peptide derived from B7-2 homodimer interface, abutted by D-Ala on both termini |
| SEQ ID NO. 26 | YMGRTSFDSD | Peptide derived from B7-2 homodimer interface |
| SEQ ID NO. 27 | (D-Ala)YMGRTSFDSD(D-Ala) | A Peptide derived from B7-2 homodimer interface, abutted by D-Ala on both termini |
| SEQ ID NO. 28 | VKEVATLS | Peptide derived from the homodimer interface of B7-1 |
| SEQ ID NO. 29 | (D-Ala)VKEVATLS(D-Ala) | Peptide derived from B7-1 homodimer interface, abutted by D-Ala on both termini |
| SEQ ID NO. 30 | VEELAQTR | Peptide derived from B7-1 homodimer interface |
| SEQ ID NO. 31 | (D-Ala)VEELAQTR(D-Ala) | Peptide derived from B7-1 homodimer interface, abutted by D-Ala on both termini |
| SEQ ID NO. 32 | MSGDMNIW | Peptide derived from B7-1 homodimer interface |
| SEQ ID NO. 33 | (D-Ala)MSGDMNIW(D-Ala) | Peptide derived from B7-1 homodimer interface, abutted by D-Ala on both termini |
| SEQ ID NO. 34 | SIVILALR | Peptide derived from B7-1 homodimer interface |
| SEQ ID NO. 35 | (D-Ala)SIVILALR(D-Ala) | Peptide derived from B7-1 homodimer interface, abutted by D-Ala on both termini |
| SEQ ID NO. 36 | YKNRTIFDIT | Peptide derived from B7-1 homodimer interface |

TABLE 3-continued

Sequences referred to herein

| SEQ ID NO. | Sequence | Description |
|---|---|---|
| SEQ ID NO. 37 | (D-Ala)YKNRTIFDIT(D-Ala) | Peptide derived from B7-1 homodimer interface, abutted by D-Ala on both termini |
| SEQ ID NO. 38 | MNIWPEYK | pB1-4, derived from B7-1 homodimer interface |
| SEQ ID NO. 39 | (D-Ala)MNIWPEYK(D-Ala) | pB1-4, derived from B7-1 homodimer interface, abutted by D-Ala on both termini |
| SEQ ID NO. 40 | KNRTIFDITN | pB1-7, derived from B7-1 homodimer interface |
| SEQ ID NO. 41 | (D-Ala)KNRTIFDITN(D-Ala) | pB1-7, derived from B7-1 homodimer interface, abutted by D-Ala on both termini |
| SEQ ID NO. 42 | DITNNLSIV | pB1-6, derived from B7-1 homodimer interface |
| SEQ ID NO. 43 | (D-Ala)DITNNLSIV(D-Ala) | pB1-6, derived from B7-1 homodimer interface, abutted by D-Ala on both termini |
| SEQ ID NO. 44 | LGKEKFDSVHSKYMGRTSFDSDSWTLRLHN | Peptide derived from B7-2 homodimer interface |
| SEQ ID NO. 45 | (D-Ala)LGKEKFDSVHSKYMGRTSFDSDSWTLRLHN(D-Ala) | A Peptide derived from B7-2 homodimer interface, abutted by D-Ala on both termini |
| SEQ ID NO. 46 | SGDMNIWPEYKNRTIFDITNNLSIVILA | Peptide derived from B7-1 homodimer interface |
| SEQ ID NO. 47 | (D-Ala)SGDMNIWPEYKNRTIFDITNNLSIVILA(D-Ala) | Peptide derived from B7-1 homodimer interface, abutted by D-Ala on both termini |
| SEQ ID NO. 48 | YKNRTIFD | Peptide derived from B7-1 homodimer interface pB1-8 |
| SEQ ID NO. 49 | (D-Ala)YKNRTIFD(D-Ala) | Peptide derived from B7-1 homodimer interface, abutted by D-Ala on both termini D-Ala-pB1-8 |
| SEQ ID NO. 50 | MLKIQAYFNE TADLPCQFAN SQNQSLSELV VFWQDQENLV LNEVYLGKEK FDSVHSKYMG RTSFDSDSWT LRLHNLQIKD KGLYQCIIHH KKPTGMIRIH QMNSELSVLA | Variant of SEQ ID NO. 13, in which N-terminal P is replaced by M (underlined) |
| SEQ IN NO. 57 | MNIWPEYKNRTIFDITNNLSIV | Fragment of hB7-1; see FIGS. 11 and 12 |
| SEQ ID NO. 58 | EKFDSVHSKYMGRTSFDSDSWTLR | Fragment of hB7-2, see FIG. 12 |

TABLE 3-continued

Sequences referred to herein

| SEQ ID NO. | Sequence | Description |
|---|---|---|
| SEQ ID NO. 59 | MYPPPY | Fragment of human CD28 |

The invention claimed is:

1. An isolated and purified peptide consisting of the amino acid sequence selected from the group consisting of SEQ ID NO:38 (MNIWPEYK, also designated as peptide pB1-4), SEQ ID NO:40 (KNRTIFDITN, also designated as peptide pB1-7), SEQ ID NO:42 (DITNNLSIV, also designated as peptide pB1-6), SEQ ID NO:46 (SGDMNIWPEYKNRTIFDITNNLSIVILA) and SEQ ID NO:48 (YKNRTIFD, also designated as peptide pB1-8), or a functional derivative of said amino acid sequence that is any one of:
(i) said amino acid sequence that is extended at the N terminus and/or the C terminus thereof:
 (a) by cysteine or by lauryl cysteine;
 (b) by an organic moiety that is not naturally occurring or by a non-naturally occurring amino acid residue;
 (c) by N-acetyl or lysyl-palmitoyl residue;
 (d) by hydrophobic amino acid residue(s) which is/are a naturally occurring or non-naturally occurring amino acid residue(s); or
 (e) by 1 to 4 consecutive amino acid residues present in immediately adjacent corresponding positions of the amino acid sequence denoted by SEQ ID NO: 14;
(ii) a dimer or multimer of said amino acid sequence or any of the functional derivatives of (i); or
(iii) a constrained conformation of said amino acid sequence or any of the functional derivatives of (i) or (ii), wherein the constrained conformation is formed by an internal bridge or disulfide bridge; and
pharmaceutically acceptable salts or esters of any of said peptides and functional derivatives thereof.

2. The isolated and purified peptide according to claim 1, wherein said peptide consists of the amino acid sequence of one of SEQ ID NO:38, 40, 42, 46 or 48 extended at its N terminus and/or at its C terminus by a D-Ala amino acid residue.

3. The isolated and purified peptide according to claim 2, being any one of a peptide consisting of the amino acid sequence (D-A)MNIWPEYK(D-A) (SEQ ID NO: 39, also designated as peptide D-Ala-pB1-4), a peptide consisting of the amino acid sequence (D-A)KNRTIFDITN(D-A) (SEQ ID NO:41, also designated as peptide D-Ala-pB1-7), a peptide consisting of the amino acid sequence (D-Ala)DITNNLSIV(D-Ala) (SEQ ID NO:43, also designated as peptide D-Ala-pB1-6), and a peptide consisting of the amino acid sequence (D-Ala)YKNRTIFD(D-Ala) (SEQ ID NO:49, also designated as peptide D-Ala-pB1-8), wherein (D-A) in the amino acid sequence is D-alanine.

4. A pharmaceutical composition comprising as an active ingredient at least one isolated and purified peptide as defined in claim 1, optionally further comprising a pharmaceutically acceptable carrier, diluent, adjuvant and/or excipient.

5. A pharmaceutical composition comprising as an active ingredient at least one isolated and purified peptide as defined in claim 3, optionally further comprising a pharmaceutically acceptable carrier, diluent, adjuvant and/or excipient.

* * * * *

SEQUENCE LISTING

<160> NUMBER OF SEQ ID NOS: 59

<210> SEQ ID NO 1
<211> LENGTH: 11
<212> TYPE: PRT
<213> ORGANISM: Artificial Sequence
<220> FEATURE:
<223> OTHER INFORMATION: pB2-2
<220> FEATURE:
<221> NAME/KEY: misc_feature
<223> OTHER INFORMATION: Synthetic

<400> SEQUENCE: 1

Asp Leu Pro Cys Gln Phe Ala Asn Ser Gln Asn
1               5                   10

<210> SEQ ID NO 2
<211> LENGTH: 13
<212> TYPE: PRT
<213> ORGANISM: Artificial Sequence
<220> FEATURE:
<223> OTHER INFORMATION: D-Ala-pB2-2
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals to D-Ala
<220> FEATURE:
<221> NAME/KEY: MISC_FEATURE
<222> LOCATION: (13)..(13)
<223> OTHER INFORMATION: x equals to D-Ala

<400> SEQUENCE: 2

Xaa Asp Leu Pro Cys Gln Phe Ala Asn Ser Gln Asn Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: pB2-3
<220> FEATURE:
<221> NAME/KEY: misc_feature
<223> OTHER INFORMATION: Synthetic

<400> SEQUENCE: 3

His His Lys Lys Pro Thr Gly Met Ile Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D-Ala-pB2-3

```
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equal to D-Ala
<220> FEATURE:
<221> NAME/KEY: MISC_FEATURE
<222> LOCATION: (12)..(12)
<223> OTHER INFORMATION: x equal to D-Ala

<400> SEQUENCE: 4

Xaa His His Lys Lys Pro Thr Gly Met Ile Arg Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: pB2-4
<220> FEATURE:
<221> NAME/KEY: misc_feature
<223> OTHER INFORMATION: Synthetic

<400> SEQUENCE: 5

Glu Lys Phe Asp Ser Val His Ser Lys Tyr Met
1               5                   10

<210> SEQ ID NO 6
<211> LENGTH: 13
<212> TYPE: PRT
<213> ORGANISM: Artificial Sequence
<220> FEATURE:
<223> OTHER INFORMATION: D-Ala-pB2-4
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equal to D-Ala
<220> FEATURE:
<221> NAME/KEY: MISC_FEATURE
<222> LOCATION: (13)..(13)
<223> OTHER INFORMATION: x equal to D-Ala

<400> SEQUENCE: 6

Xaa Glu Lys Phe Asp Ser Val His Ser Lys Tyr Met Xaa
1               5                   10

<210> SEQ ID NO 7
<211> LENGTH: 7
<212> TYPE: PRT
<213> ORGANISM: Artificial Sequence
<220> FEATURE:
<223> OTHER INFORMATION: pB2-5
<220> FEATURE:
<221> NAME/KEY: misc_feature
<223> OTHER INFORMATION: Synthetic

<400> SEQUENCE: 7

Met Leu Lys Ile Gln Ala Tyr
1               5

<210> SEQ ID NO 8
<211> LENGTH: 9
<212> TYPE: PRT
<213> ORGANISM: Artificial Sequence
<220> FEATURE:
```

```
<223> OTHER INFORMATION: D-Ala-pB2-5
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equal to D-Ala
<220> FEATURE:
<221> NAME/KEY: MISC_FEATURE
<222> LOCATION: (9)..(9)
<223> OTHER INFORMATION: x equal to D-Ala

<400> SEQUENCE: 8

Xaa Met Leu Lys Ile Gln Ala Tyr Xaa
1               5

<210> SEQ ID NO 9
<211> LENGTH: 8
<212> TYPE: PRT
<213> ORGANISM: Artificial Sequence
<220> FEATURE:
<223> OTHER INFORMATION: pB2-6
<220> FEATURE:
<221> NAME/KEY: misc_feature
<223> OTHER INFORMATION: Synthetic

<400> SEQUENCE: 9

Asp Ser Asp Ser Trp Thr Leu Arg
1               5

<210> SEQ ID NO 10
<211> LENGTH: 10
<212> TYPE: PRT
<213> ORGANISM: Artificial Sequence
<220> FEATURE:
<223> OTHER INFORMATION: D-Ala-pB2-6
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equal to D-Ala
<220> FEATURE:
<221> NAME/KEY: MISC_FEATURE
<222> LOCATION: (10)..(10)
<223> OTHER INFORMATION: x equal to D-Ala

<400> SEQUENCE: 10

Xaa Asp Ser Asp Ser Trp Thr Leu Arg Xaa
1               5                   10

<210> SEQ ID NO 11
<211> LENGTH: 10
<212> TYPE: PRT
<213> ORGANISM: Artificial Sequence
<220> FEATURE:
<223> OTHER INFORMATION: pB2-7
<220> FEATURE:
<221> NAME/KEY: misc_feature
<223> OTHER INFORMATION: Synthetic

<400> SEQUENCE: 11

Met Gly Arg Thr Ser Phe Asp Ser Asp Ser
1               5                   10

<210> SEQ ID NO 12
<211> LENGTH: 12
<212> TYPE: PRT
<213> ORGANISM: Artificial Sequence
```

```
<220> FEATURE:
<223> OTHER INFORMATION: D-Ala-pB2-7
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals to D-Ala
<220> FEATURE:
<221> NAME/KEY: MISC_FEATURE
<222> LOCATION: (12)..(12)
<223> OTHER INFORMATION: x equals to D-Ala

<400> SEQUENCE: 12

Xaa Met Gly Arg Thr Ser Phe Asp Ser Asp Ser Xaa
1               5                   10

<210> SEQ ID NO 13
<211> LENGTH: 110
<212> TYPE: PRT
<213> ORGANISM: Homo sapiens

<400> SEQUENCE: 13

Pro Leu Lys Ile Gln Ala Tyr Phe Asn Glu Thr Ala Asp Leu Pro Cys
1               5                   10                  15

Gln Phe Ala Asn Ser Gln Asn Gln Ser Leu Ser Glu Leu Val Val Phe
            20                  25                  30

Trp Gln Asp Gln Glu Asn Leu Val Leu Asn Glu Val Tyr Leu Gly Lys
        35                  40                  45

Glu Lys Phe Asp Ser Val His Ser Lys Tyr Met Gly Arg Thr Ser Phe
    50                  55                  60

Asp Ser Asp Ser Trp Thr Leu Arg Leu His Asn Leu Gln Ile Lys Asp
65                  70                  75                  80

Lys Gly Leu Tyr Gln Cys Ile Ile His His Lys Pro Thr Gly Met
                85                  90                  95

Ile Arg Ile His Gln Met Asn Ser Glu Leu Ser Val Leu Ala
            100                 105                 110

<210> SEQ ID NO 14
<211> LENGTH: 110
<212> TYPE: PRT
<213> ORGANISM: Homo sapiens

<400> SEQUENCE: 14

Phe Cys Ser Gly Val Ile His Val Thr Lys Glu Val Lys Glu Val Ala
1               5                   10                  15

Thr Leu Ser Cys Gly His Asn Val Ser Val Glu Glu Leu Ala Gln Thr
            20                  25                  30

Arg Ile Tyr Trp Gln Lys Glu Lys Lys Met Val Leu Thr Met Met Ser
        35                  40                  45

Gly Asp Met Asn Ile Trp Pro Glu Tyr Lys Asn Arg Thr Ile Phe Asp
    50                  55                  60

Ile Thr Asn Asn Leu Ser Ile Val Ile Leu Ala Leu Arg Pro Ser Asp
65                  70                  75                  80

Glu Gly Thr Tyr Glu Cys Val Val Leu Lys Tyr Glu Lys Asp Ala Phe
                85                  90                  95

Lys Arg Glu His Leu Ala Glu Val Thr Leu Ser Val Lys Ala
            100                 105                 110

<210> SEQ ID NO 15
```

```
<211> LENGTH: 12
<212> TYPE: PRT
<213> ORGANISM: Artificial Sequence
<220> FEATURE:
<223> OTHER INFORMATION: p12A
<220> FEATURE:
<221> NAME/KEY: misc_feature
<223> OTHER INFORMATION: Synthetic

<400> SEQUENCE: 15

Tyr Asn Lys Lys Lys Ala Thr Val Gln Glu Leu Asp
1               5                   10

<210> SEQ ID NO 16
<211> LENGTH: 8
<212> TYPE: PRT
<213> ORGANISM: Artificial Sequence
<220> FEATURE:
<223> OTHER INFORMATION: p2TA
<220> FEATURE:
<221> NAME/KEY: misc_feature
<223> OTHER INFORMATION: Synthetic

<400> SEQUENCE: 16

Ser Pro Met Leu Val Ala Tyr Asp
1               5

<210> SEQ ID NO 17
<211> LENGTH: 9
<212> TYPE: PRT
<213> ORGANISM: Artificial Sequence
<220> FEATURE:
<223> OTHER INFORMATION: p1TA
<220> FEATURE:
<221> NAME/KEY: misc_feature
<223> OTHER INFORMATION: Synthetic

<400> SEQUENCE: 17

His Val Lys Gly Lys His Leu Cys Pro
1               5

<210> SEQ ID NO 18
<211> LENGTH: 8
<212> TYPE: PRT
<213> ORGANISM: Artificial Sequence
<220> FEATURE:
<223> OTHER INFORMATION: A peptide derived from B7-2 homodimer interface
<220> FEATURE:
<221> NAME/KEY: misc_feature
<223> OTHER INFORMATION: Synthetic

<400> SEQUENCE: 18

Phe Asn Glu Thr Ala Asp Leu Pro
1               5

<210> SEQ ID NO 19
<211> LENGTH: 10
<212> TYPE: PRT
<213> ORGANISM: Artificial Sequence
<220> FEATURE:
<223> OTHER INFORMATION: A peptide derived from B7-2 homodimer
      interface, abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals to D-Ala
<220> FEATURE:
<221> NAME/KEY: MISC_FEATURE
```

```
<222> LOCATION: (10)..(10)
<223> OTHER INFORMATION: x equals to D-Ala

<400> SEQUENCE: 19

Xaa Phe Asn Glu Thr Ala Asp Leu Pro Xaa
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Peptide derived from B7-2 homodimer interface
<220> FEATURE:
<221> NAME/KEY: misc_feature
<223> OTHER INFORMATION: Synthetic

<400> SEQUENCE: 20

Asn Gln Ser Leu Ser Glu Leu Val
1               5

<210> SEQ ID NO 21
<211> LENGTH: 10
<212> TYPE: PRT
<213> ORGANISM: Artificial Sequence
<220> FEATURE:
<223> OTHER INFORMATION: A Peptide derived from B7-2 homodimer
      interface, abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals to D-Ala
<220> FEATURE:
<221> NAME/KEY: MISC_FEATURE
<222> LOCATION: (10)..(10)
<223> OTHER INFORMATION: x equals to D-Ala

<400> SEQUENCE: 21

Xaa Asn Gln Ser Leu Ser Glu Leu Val Xaa
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Peptide derived from B7-2 homodimer interface
<220> FEATURE:
<221> NAME/KEY: misc_feature
<223> OTHER INFORMATION: Synthetic

<400> SEQUENCE: 22

Tyr Leu Gly Lys Glu Lys Phe Asp
1               5

<210> SEQ ID NO 23
<211> LENGTH: 10
<212> TYPE: PRT
<213> ORGANISM: Artificial Sequence
<220> FEATURE:
<223> OTHER INFORMATION: Peptide derived from B7-2 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
```

```
<223> OTHER INFORMATION: x equals to D-Ala
<220> FEATURE:
<221> NAME/KEY: MISC_FEATURE
<222> LOCATION: (10)..(10)
<223> OTHER INFORMATION: x equals to D-Ala

<400> SEQUENCE: 23

Xaa Tyr Leu Gly Lys Glu Lys Phe Asp Xaa
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Peptide derived from B7-2 homodimer interface
<220> FEATURE:
<221> NAME/KEY: misc_feature
<223> OTHER INFORMATION: Synthetic

<400> SEQUENCE: 24

Thr Leu Arg Leu His Asn Leu Gln
1               5

<210> SEQ ID NO 25
<211> LENGTH: 10
<212> TYPE: PRT
<213> ORGANISM: Artificial Sequence
<220> FEATURE:
<223> OTHER INFORMATION: Peptide derived from B7-2 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals to D-Ala
<220> FEATURE:
<221> NAME/KEY: MISC_FEATURE
<222> LOCATION: (10)..(10)
<223> OTHER INFORMATION: x equals to D-Ala

<400> SEQUENCE: 25

Xaa Thr Leu Arg Leu His Asn Leu Gln Xaa
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Peptide derived from B7-2 homodimer interface
<220> FEATURE:
<221> NAME/KEY: misc_feature
<223> OTHER INFORMATION: Synthetic

<400> SEQUENCE: 26

Tyr Met Gly Arg Thr Ser Phe Asp Ser Asp
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Peptide derived from B7-2 homodimer interface,
      abutted by D-Ala on both termini
<220> FEATURE:
<221> NAME/KEY: misc_feature
<223> OTHER INFORMATION: Synthetic
```

```
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (12)..(12)
<223> OTHER INFORMATION: x equals D-Ala

<400> SEQUENCE: 27

Xaa Tyr Met Gly Arg Thr Ser Phe Asp Ser Asp Xaa
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Peptide derived from the homodimer interface of
      B7-1
<220> FEATURE:
<221> NAME/KEY: misc_feature
<223> OTHER INFORMATION: Synthetic

<400> SEQUENCE: 28

Val Lys Glu Val Ala Thr Leu Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Peptide derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala

<400> SEQUENCE: 29

Xaa Val Lys Glu Val Ala Thr Leu Ser Xaa
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Peptide derived from B7-1 homodimer interface
<220> FEATURE:
<221> NAME/KEY: misc_feature
<223> OTHER INFORMATION: Synthetic

<400> SEQUENCE: 30

Val Glu Glu Leu Ala Gln Thr Arg
1               5

<210> SEQ ID NO 31
<211> LENGTH: 10
<212> TYPE: PRT
<213> ORGANISM: Artificial Sequence
<220> FEATURE:
<223> OTHER INFORMATION: Peptide derived from B7-1 homodimer interface,
```

```
         abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala

<400> SEQUENCE: 31

Xaa Val Glu Glu Leu Ala Gln Thr Arg Xaa
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Peptide derived from B7-1 homodimer interface
<220> FEATURE:
<221> NAME/KEY: misc_feature
<223> OTHER INFORMATION: Synthetic

<400> SEQUENCE: 32

Met Ser Gly Asp Met Asn Ile Trp
1               5

<210> SEQ ID NO 33
<211> LENGTH: 10
<212> TYPE: PRT
<213> ORGANISM: Artificial Sequence
<220> FEATURE:
<223> OTHER INFORMATION: Peptide derived from B7-1 homodimer interface,
         abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala

<400> SEQUENCE: 33

Xaa Met Ser Gly Asp Met Asn Ile Trp Xaa
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Peptide derived from B7-1 homodimer interface
<220> FEATURE:
<221> NAME/KEY: misc_feature
<223> OTHER INFORMATION: Synthetic

<400> SEQUENCE: 34

Ser Ile Val Ile Leu Ala Leu Arg
1               5

<210> SEQ ID NO 35
<211> LENGTH: 10
<212> TYPE: PRT
```

```
<213> ORGANISM: Artificial Sequence
<220> FEATURE:
<223> OTHER INFORMATION: Peptide derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala

<400> SEQUENCE: 35

Xaa Ser Ile Val Ile Leu Ala Leu Arg Xaa
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Peptide derived from B7-1 homodimer interface
<220> FEATURE:
<221> NAME/KEY: misc_feature
<223> OTHER INFORMATION: Synthetic

<400> SEQUENCE: 36

Tyr Lys Asn Arg Thr Ile Phe Asp Ile Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Peptide derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (12)..(12)
<223> OTHER INFORMATION: x equals D-Ala

<400> SEQUENCE: 37

Xaa Tyr Lys Asn Arg Thr Ile Phe Asp Ile Thr Xaa
1               5                   10

<210> SEQ ID NO 38
<211> LENGTH: 8
<212> TYPE: PRT
<213> ORGANISM: Artificial Sequence
<220> FEATURE:
<223> OTHER INFORMATION: pB1-4, derived from B7-1 homodimer interface
<220> FEATURE:
<221> NAME/KEY: misc_feature
<223> OTHER INFORMATION: Synthetic

<400> SEQUENCE: 38

Met Asn Ile Trp Pro Glu Tyr Lys
1               5
```

```
<210> SEQ ID NO 39
<211> LENGTH: 10
<212> TYPE: PRT
<213> ORGANISM: Artificial Sequence
<220> FEATURE:
<223> OTHER INFORMATION: pB1-4, derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala

<400> SEQUENCE: 39

Xaa Met Asn Ile Trp Pro Glu Tyr Lys Xaa
1               5                   10

<210> SEQ ID NO 40
<211> LENGTH: 10
<212> TYPE: PRT
<213> ORGANISM: Artificial Sequence
<220> FEATURE:
<223> OTHER INFORMATION: pB1-7, derived from B7-1 homodimer interface
<220> FEATURE:
<221> NAME/KEY: misc_feature
<223> OTHER INFORMATION: Synthetic

<400> SEQUENCE: 40

Lys Asn Arg Thr Ile Phe Asp Ile Thr Asn
1               5                   10

<210> SEQ ID NO 41
<211> LENGTH: 12
<212> TYPE: PRT
<213> ORGANISM: Artificial Sequence
<220> FEATURE:
<223> OTHER INFORMATION: pB1-7, derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (12)..(12)
<223> OTHER INFORMATION: x equals D-Ala

<400> SEQUENCE: 41

Xaa Lys Asn Arg Thr Ile Phe Asp Ile Thr Asn Xaa
1               5                   10

<210> SEQ ID NO 42
<211> LENGTH: 9
<212> TYPE: PRT
<213> ORGANISM: Artificial Sequence
<220> FEATURE:
<223> OTHER INFORMATION: pB1-6, derived from B7-1 homodimer interface
<220> FEATURE:
<221> NAME/KEY: misc_feature
<223> OTHER INFORMATION: Synthetic

<400> SEQUENCE: 42

Asp Ile Thr Asn Asn Leu Ser Ile Val
```

```
<210> SEQ ID NO 43
<211> LENGTH: 11
<212> TYPE: PRT
<213> ORGANISM: Artificial Sequence
<220> FEATURE:
<223> OTHER INFORMATION: pB1-6, derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (11)..(11)
<223> OTHER INFORMATION: x equals D-Ala

<400> SEQUENCE: 43

Xaa Asp Ile Thr Asn Asn Leu Ser Ile Val Xaa
1               5                   10

<210> SEQ ID NO 44
<211> LENGTH: 30
<212> TYPE: PRT
<213> ORGANISM: Artificial Sequence
<220> FEATURE:
<223> OTHER INFORMATION: Peptide derived from B7-2 homodimer interface
<220> FEATURE:
<221> NAME/KEY: misc_feature
<223> OTHER INFORMATION: Synthetic

<400> SEQUENCE: 44

Leu Gly Lys Glu Lys Phe Asp Ser Val His Ser Lys Tyr Met Gly Arg
1               5                   10                  15

Thr Ser Phe Asp Ser Asp Ser Trp Thr Leu Arg Leu His Asn
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: A Peptide derived from B7-2 homodimer
      interface, abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (32)..(32)
<223> OTHER INFORMATION: x equals D-Ala

<400> SEQUENCE: 45

Xaa Leu Gly Lys Glu Lys Phe Asp Ser Val His Ser Lys Tyr Met Gly
1               5                   10                  15

Arg Thr Ser Phe Asp Ser Asp Ser Trp Thr Leu Arg Leu His Asn Xaa
            20                  25                  30

<210> SEQ ID NO 46
<211> LENGTH: 28
<212> TYPE: PRT
<213> ORGANISM: Artificial Sequence
```

```
<220> FEATURE:
<223> OTHER INFORMATION: Peptide derived from B7-1 homodimer interface
<220> FEATURE:
<221> NAME/KEY: misc_feature
<223> OTHER INFORMATION: Synthetic

<400> SEQUENCE: 46

Ser Gly Asp Met Asn Ile Trp Pro Glu Tyr Lys Asn Arg Thr Ile Phe
1               5                   10                  15

Asp Ile Thr Asn Asn Leu Ser Ile Val Ile Leu Ala
            20                  25

<210> SEQ ID NO 47
<211> LENGTH: 30
<212> TYPE: PRT
<213> ORGANISM: Artificial Sequence
<220> FEATURE:
<223> OTHER INFORMATION: Peptide derived from B7-1 homodimer interface,
      abutted by D-Ala on both termini
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (30)..(30)
<223> OTHER INFORMATION: x equals D-Ala

<400> SEQUENCE: 47

Xaa Ser Gly Asp Met Asn Ile Trp Pro Glu Tyr Lys Asn Arg Thr Ile
1               5                   10                  15

Phe Asp Ile Thr Asn Asn Leu Ser Ile Val Ile Leu Ala Xaa
            20                  25                  30

<210> SEQ ID NO 48
<211> LENGTH: 8
<212> TYPE: PRT
<213> ORGANISM: Artificial Sequence
<220> FEATURE:
<223> OTHER INFORMATION: Peptide derived from B7-1 homodimer interface
      pB1-8
<220> FEATURE:
<221> NAME/KEY: misc_feature
<223> OTHER INFORMATION: Synthetic

<400> SEQUENCE: 48

Tyr Lys Asn Arg Thr Ile Phe Asp
1               5

<210> SEQ ID NO 49
<211> LENGTH: 10
<212> TYPE: PRT
<213> ORGANISM: Artificial Sequence
<220> FEATURE:
<223> OTHER INFORMATION: Peptide derived from B7-1 homodimer interface,
      abutted by D-Ala on both termini D-Ala-pB1-8
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: x equals D-Ala
<220> FEATURE:
<221> NAME/KEY: MISC_FEATURE
<222> LOCATION: (10)..(10)
<223> OTHER INFORMATION: x equals D-Ala
```

```
<400> SEQUENCE: 49

Xaa Tyr Lys Asn Arg Thr Ile Phe Asp Xaa
1               5                   10

<210> SEQ ID NO 50
<211> LENGTH: 110
<212> TYPE: PRT
<213> ORGANISM: Artificial Sequence
<220> FEATURE:
<223> OTHER INFORMATION: Variant of SEQ ID NO. 13, in which N-terminal P
      is replaced by M
<220> FEATURE:
<221> NAME/KEY: misc_feature
<223> OTHER INFORMATION: Synthetic

<400> SEQUENCE: 50

Met Leu Lys Ile Gln Ala Tyr Phe Asn Glu Thr Ala Asp Leu Pro Cys
1               5                   10                  15

Gln Phe Ala Asn Ser Gln Asn Gln Ser Leu Ser Glu Leu Val Val Phe
            20                  25                  30

Trp Gln Asp Gln Glu Asn Leu Val Leu Asn Glu Val Tyr Leu Gly Lys
        35                  40                  45

Glu Lys Phe Asp Ser Val His Ser Lys Tyr Met Gly Arg Thr Ser Phe
    50                  55                  60

Asp Ser Asp Ser Trp Thr Leu Arg Leu His Asn Leu Gln Ile Lys Asp
65                  70                  75                  80

Lys Gly Leu Tyr Gln Cys Ile Ile His His Lys Lys Pro Thr Gly Met
                85                  90                  95

Ile Arg Ile His Gln Met Asn Ser Glu Leu Ser Val Leu Ala
            100                 105                 110

<210> SEQ ID NO 51
<211> LENGTH: 27
<212> TYPE: DNA
<213> ORGANISM: Artificial Sequence
<220> FEATURE:
<223> OTHER INFORMATION: Primer for B7-2 cloning
<220> FEATURE:
<221> NAME/KEY: misc_feature
<223> OTHER INFORMATION: Synthetic

<400> SEQUENCE: 51
gacgtcgacg gaaggcttgc acagggt                                          27

<210> SEQ ID NO 52
<211> LENGTH: 32
<212> TYPE: DNA
<213> ORGANISM: Artificial Sequence
<220> FEATURE:
<223> OTHER INFORMATION: Primer for B7-2 cloning
<220> FEATURE:
<221> NAME/KEY: misc_feature
<223> OTHER INFORMATION: Synthetic

<400> SEQUENCE: 52
cacgcggccg cccaggtcat gagccattaa gc                                    32

<210> SEQ ID NO 53
<211> LENGTH: 27
<212> TYPE: DNA
<213> ORGANISM: Artificial Sequence
<220> FEATURE:
<223> OTHER INFORMATION: Primer for preparing B7-2-GFP fusion construct
<220> FEATURE:
<221> NAME/KEY: misc_feature
```

<223> OTHER INFORMATION: Synthetic

<400> SEQUENCE: 53
tactcgagat gggactgagt aacattc 27

<210> SEQ ID NO 54
<211> LENGTH: 30
<212> TYPE: DNA
<213> ORGANISM: Artificial Sequence
<220> FEATURE:
<223> OTHER INFORMATION: Primer for preparing B7-2-GFP fusion construct
<220> FEATURE:
<221> NAME/KEY: misc_feature
<223> OTHER INFORMATION: Synthetic

<400> SEQUENCE: 54
gtccgcggtg aagcatgtac acttttgtcg 30

<210> SEQ ID NO 55
<211> LENGTH: 17
<212> TYPE: DNA
<213> ORGANISM: Artificial Sequence
<220> FEATURE:
<223> OTHER INFORMATION: Primer for preparing B7-2C/Cherry vector
<220> FEATURE:
<221> NAME/KEY: misc_feature
<223> OTHER INFORMATION: Synthetic

<400> SEQUENCE: 55
gtctctcgtc cttccgg 17

<210> SEQ ID NO 56
<211> LENGTH: 18
<212> TYPE: DNA
<213> ORGANISM: Artificial Sequence
<220> FEATURE:
<223> OTHER INFORMATION: Primer for preparing B7-2C/Cherry vector
<220> FEATURE:
<221> NAME/KEY: misc_feature
<223> OTHER INFORMATION: Synthetic

<400> SEQUENCE: 56
ctaacttcag tcaacctg 18

<210> SEQ ID NO 57
<211> LENGTH: 22
<212> TYPE: PRT
<213> ORGANISM: Homo sapiens
<220> FEATURE:
<221> NAME/KEY: misc_feature
<223> OTHER INFORMATION: Synthetic

<400> SEQUENCE: 57

Met Asn Ile Trp Pro Glu Tyr Lys Asn Arg Thr Ile Phe Asp Ile Thr
1               5                   10                  15

Asn Asn Leu Ser Ile Val
            20

<210> SEQ ID NO 58
<211> LENGTH: 24
<212> TYPE: PRT
<213> ORGANISM: Homo sapiens
<220> FEATURE:
<221> NAME/KEY: misc_feature
<223> OTHER INFORMATION: Synthetic

<400> SEQUENCE: 58

```
Glu Lys Phe Asp Ser Val His Ser Lys Tyr Met Gly Arg Thr Ser Phe
1               5                   10                  15

Asp Ser Asp Ser Trp Thr Leu Arg
                20

<210> SEQ ID NO 59
<211> LENGTH: 6
<212> TYPE: PRT
<213> ORGANISM: Homo sapiens
<220> FEATURE:
<221> NAME/KEY: misc_feature
<223> OTHER INFORMATION: Synthetic

<400> SEQUENCE: 59

Met Tyr Pro Pro Pro Tyr
1               5
```